(12) United States Patent
Smith et al.

(10) Patent No.: US 10,071,947 B2
(45) Date of Patent: Sep. 11, 2018

(54) PURIFICATION OF LONG CHAIN DIACIDS

(71) Applicant: INVISTA North America S.à.r.l., Wilmington, DE (US)

(72) Inventors: Gary J. Smith, Wilton (GB); Paul S. Pearlman, Thornton, PA (US); Gregory S. Kirby, Avondale, PA (US)

(73) Assignee: INVISTA North America S.à.r.l., Wilmington, DE (US)

( * ) Notice: Subject to any disclaimer, the term of this patent is extended or adjusted under 35 U.S.C. 154(b) by 0 days.

(21) Appl. No.: 14/842,696

(22) Filed: Sep. 1, 2015

(65) Prior Publication Data

US 2016/0159723 A1    Jun. 9, 2016

Related U.S. Application Data

(60) Provisional application No. 62/044,822, filed on Sep. 2, 2014, provisional application No. 62/194,024, filed on Jul. 17, 2015.

(51) Int. Cl.

| | |
|---|---|
| *C07C 59/245* | (2006.01) |
| *C07C 51/42* | (2006.01) |
| *B01D 15/18* | (2006.01) |
| *C07C 51/47* | (2006.01) |
| *B01D 15/02* | (2006.01) |
| *B01D 15/22* | (2006.01) |
| *C07C 55/02* | (2006.01) |
| *C07C 55/21* | (2006.01) |

(52) U.S. Cl.
CPC ............. *C07C 51/42* (2013.01); *B01D 15/02* (2013.01); *B01D 15/185* (2013.01); *B01D 15/1892* (2013.01); *B01D 15/22* (2013.01); *C07C 51/47* (2013.01); *C07C 55/02* (2013.01); *C07C 55/21* (2013.01)

(58) Field of Classification Search
CPC ...................................................... C07C 51/42
USPC ............................................................ 562/582
See application file for complete search history.

(56) References Cited

U.S. PATENT DOCUMENTS

| | | | |
|---|---|---|---|
| 2,985,589 | A | 5/1961 | Broughton et al. |
| 3,696,107 | A | 10/1972 | Neuzil |
| 3,706,812 | A | 12/1972 | Derosset et al. |
| 3,761,533 | A | 9/1973 | Otani et al. |
| 4,764,276 | A | 8/1988 | Berry et al. |
| 5,069,883 | A | 12/1991 | Matonte |

(Continued)

FOREIGN PATENT DOCUMENTS

| | | | | |
|---|---|---|---|---|
| CA | 2 802 951 A1 | 12/2011 | | |
| DE | 102010025167 A1 | * 12/2011 | ............. | C07C 51/47 |

(Continued)

OTHER PUBLICATIONS

PCT International Preliminary Report on Patentability dated Mar. 7, 2017, for International Application No. PCT/US2015/047970 (10 pages).

(Continued)

*Primary Examiner* — Deborah D Carr
(74) *Attorney, Agent, or Firm* — William J. Simmons; Thomas H. Jenkins

(57) ABSTRACT

The present disclosure relates to methods for separating and purifying a long chain diacid from other long chain diacids, monocarboxylic acids, hydroxyl acids or alkanes by simulated or actual moving bed chromatography.

15 Claims, 13 Drawing Sheets

(56) References Cited

U.S. PATENT DOCUMENTS

| | | |
|---|---|---|
| 6,979,402 B1 | 12/2005 | Sprague et al. |
| 2012/0253069 A1* | 10/2012 | Zang .................. C07C 51/47 |
| | | 562/593 |

FOREIGN PATENT DOCUMENTS

| | | |
|---|---|---|
| EP | 415821 A1 | 3/1991 |
| FR | 2103302 A5 | 4/1972 |
| FR | 2651148 A1 | 3/1991 |
| WO | WO 2013/169447 A1 | 11/2013 |

OTHER PUBLICATIONS

Machine Translation of DE 10 2010 025167 A1 (12 pages) (last accessed Nov. 6, 2017).
Catherine E. Housecroft & Alan G. Sharpe, Organic Chemistry 44-46 (Harlow, Pearson Educ. Ltd. 3d ed. 2008).
John McMurry et al., Fundamentals of General, Organic, and Biological Chemistry 128 (Upper Saddle River, Pearson Educ., Inc. 5th ed. 2007).

* cited by examiner

PURIFICATION OF LONG CHAIN DIACIDS

RELATED APPLICATIONS

This application claims priority from U.S. Provisional application Ser. Nos. 62/044,822, filed Sep. 2, 2015 and 62/194,024, filed Jul. 17, 2015, the entire contents of which are incorporated by reference herein in their entirety.

FIELD OF THE INVENTION

The invention relates to methods for separating and purifying a long chain diacid from other long chain diacids, monocarboxylic acids, hydroxyl acids or alkanes by simulated or actual moving bed chromatography.

BACKGROUND OF THE TECHNOLOGY

Dicarboxylic acids comprising six or more carbon atoms are commonly referred to as "long-chain diacids". Long-chain diacids can be used as basic constituent monomer for a series of synthetic materials. Potential uses of long-chain diacids and their derivatives include, for example, production of special nylon resins, polycarbonate, powder coatings, fragrances, hot-melt adhesives and special lubricants. Long-chain diacids can also be used as plasticizers for engineering plastics and corrosion inhibitors in, for example, metal processing technology. When used as constituent monomers for production of special nylon, long-chain diacids can demonstrate some unique performance characteristics when compared to other monomers.

Commercial quantities of long-chain diacids are generally not found in nature. Certain long-chain diacids, for example adipic acid, sebacic acid and dodecanedioic acid, can be prepared via chemical methods. For example, starting with benzene or 1,3-butadiene, dodecanedioic acid can be prepared through multiple steps of chemical reactions. Sebacic acid can be prepared through the chemical conversion of castor oil. Starting with cyclohexane, adipic acid can be prepared through multiple steps of oxidation. Long-chain diacids can also be prepared via a biological method. A biological method, for example fermentation, can produce a series of long-chain diacids containing 6 through 18 carbon atoms. Some of the chemical and biological routes to diacids can result in low levels of analogous chain length monocarboxylic acids and/or hydroxyl acids as impurities. As these impurities can impact the suitability of the diacids in the desired applications, removal of the monocarboxylic acid and hydroxyl acid from the diacid is critical.

Chromatography, for example paper chromatography, gas chromatography, and high pressure liquid chromatography, can be utilized for identification and separation of long-chain diacids. The target long-chain diacid(s) and impurities have different interacting forces with the chromatograph stationary phase. Under specific eluting conditions and/or with a specific chromatograph stationary phase, the differences between the interacting forces could be large enough to achieve separation of different components. US20120253069 describes a laboratory method of using liquid chromatography with a packed bed column to separate long chain diacids from alkanes and other long chains diacids.

The process of separating a binary mixture is illustrated with reference to a single zone system as shown in FIG. 1. The concept of a simulated or actual continuous countercurrent chromatographic separation process is explained by considering a vertical chromatographic column containing stationary phase S divided into sections, more precisely into four superimposed sub-zones I, II, III and IV going from the bottom to the top of the column. The eluent is introduced at the bottom at IE by means of a pump P. The mixture of the components A and B which are to be separated is introduced at IA+B between sub-zone II and sub-zone III. An extract containing mainly B is collected at SB between sub-zone I and sub-zone II, and a raffinate containing mainly A is collected at SA between sub-zone III and sub-zone IV.

In the case of a simulated moving bed system, a simulated downward movement of the stationary phase S is caused by movement of the introduction and collection points relative to the solid phase. In the case of an actual moving bed system, downward movement of the stationary phase S is caused by movement of the various chromatographic columns relative to the introduction and collection points. In FIG. 1, eluent flows upward and mixture A+B is injected between sub-zone II and sub-zone III. The components will move according to their chromatographic interactions with the stationary phase, for example adsorption on a porous medium. The component B that exhibits stronger affinity to the stationary phase (the slower running component) will be more slowly entrained by the eluent and will follow it with delay. The component A that exhibits the weaker affinity to the stationary phase (the faster running component) will be easily entrained by the eluent. If the right set of parameters, especially the flow rate in each zone, are correctly estimated and controlled, the component A exhibiting the weaker affinity to the stationary phase will be collected between subzone III and sub-zone IV as a raffinate and the component B exhibiting the stronger affinity to the stationary phase will be collected between sub-zone I and sub-zone II as an extract.

SUMMARY OF THE INVENTION

There is a desire in industry to separate and purify long-chain diacids produced in a commercial scale biological process in a simple and low-cost way, but this is challenging because of the similar structures between impurity acids and the target products. For example, when an alkane is used as substrate to produce long-chain diacids via fermentation, a mixture of diacids with different chain lengths, monocarboxylic acids and hydroxyl acids could be produced. This complex mixture of diacids is due, in part, to the alkanes having different chain length serving as the fermentation raw material and/or due to different metabolic pathways in the microorganism used to perform the fermentation. Also, for example, when fatty acid and/or its derivatives are used as the fermentation raw material, small quantities of fatty acid and its derivatives may remain in the fermentation product broth.

Commercial applications of long-chain diacids may require them to be of very high purity with low quantities of color-inducing impurities and high heat stability. Long-chain diacids that are the basic constituent monomer for commercial nylons (e.g., polyamides) may need to have very low monocarboxylic acid content or hydroxyl acid content, because such impurities can terminate the polymerization, leading to lower molecular weight polymers, and/or cap the terminal amine of the polymer, leading to lower dyeability. The content of color-inducing impurities that may react under high temperature may also need to be very low because it may affect the color and performance of nylon.

Examples of long-chain diacids contemplated for the methods disclosed herein are polymer grade dodecanedioic acid (for example for Nylon 6,12 or Nylon 12,12), polymer grade sebacic acid (for example for Nylon 5,10 or Nylon 6,10), and polymer grade adipic acid (for example for Nylon 6,6). For these polymer-grade long-chain diacids, it is typical for impurities such as monocarboxylic acid and hydroxyl acid to be at very low content, such as in the parts per million weight (ppmw) range, such as 10,000 ppmw or less, such as 5,000 ppmw or less, such as 1,000 ppmw or less, such as 500 ppmw or less, such as 100 ppmw or less, such as 50 ppmw or less, or such as 10 ppmw or less. As another example, to comprise an ingredient in the fragrance Musk-T, tridecanedioic acid must have low impurity levels, because impurities, including different acids, can affect the fragrance of Musk-T. Therefore, it is desirable to develop commercially suitable methods for the separation and purifying a long chain diacid from other long chain diacids, monocarboxylic acids, hydroxyl acids or alkanes.

The method of the present invention allows for large scale commercial production of high purity of long chain diacid product, for example by avoiding the problems of cost associated with recrystallization of long chain diacids. The quantity of isomeric impurities present in a long chain diacid product of the present invention will depend on the amount of impurities or additional undesired long chain diacids present in the feed mixture. The invention disclosed herein provides commercially suitable methods for the separation and purifying a long chain diacid from other long chain diacids, monocarboxylic acids, hydroxyl acids or alkanes by simulated moving bed chromatography. The long chain diacid product can comprise at least one long-chain diacid comprising an α, ω-aliphatic diacid with the main chain comprising 6 or more carbon atoms, or comprising 8 or more carbon atoms, for example, alkane diacids and olefin diacids comprising from 6 to 18 carbons. For example, the long chain diacid can be C6 diacid (adipic acid), C7 diacid (pimelic acid), C8 diacid (suberic acid), C9 diacid (azelaic acid), C10 diacid (sebacic acid), C11 diacid (undecanedioic acid), C12 diacid (dodecanedioic acid), C13 diacid (tridecanedioic acid), C14 diacid (tetradecanedioic acid), C15 diacid (pentadecanedioic acid), C16 diacid (hexadecanedioic acid), C17 diacid (heptadecanedioic acid), C18 diacid (octadecanedioic acid), or C6-18-olefin diacid. In some aspects, the at least one long-chain diacid can be one single long-chain diacid, or a mixture of different long-chain diacids. In one aspect, the long chain diacid product can be adipic acid, sebacic acid or dodecanedioic acid. In another aspect, the long chain diacid product can be produced via chemical methods. In yet another aspect, the long chain diacid is produced by fermentation of long chain alkanes, fatty acids, or fatty acid esters.

In one aspect, the hydroxyl acid impurities can be ω-hydroxyacids such as co-hydroxycaproic acid in the C-6 adipic acid case, ω-hydroxydecanoic acid in the C-10 sebacic acid case, and/or ω-hydroxydodecanoic acid in the C-12 dodecanedioic acid acid case.

In one aspect, the method of the present invention comprises a plurality of separation zones. In another aspect, two or more separation zones are used. In yet another aspect, there are 2 to 5 separation zones. Typically, the components separated in each zone have different polarities. Each zone contains an eluent, for example an aqueous alcohol, comprising various water:alcohol ratios, and/or a recycle stream comprising the extract and/or raffinate streams recycled back into the same zone. The eluent and/or recycle stream can be adjusted such that the long chain diacid product can be separated from different components of the feed mixture in each zone.

In another aspect, the present invention relates to compositions comprising a long chain diacid product, for example one obtainable by the method of the present invention.

In one aspect, this disclosure features a method for separating a LCDA (e.g., a C6- to C18-carbon diacid) from at least one impurity in a solution, the method comprising (a) introducing a feed stream comprising a solution comprising at least one 6- to 18-carbon diacid and at least one impurity, the at least one impurity comprising a component more polar than the diacid, a component less polar than the diacid, or both, into a first zone of moving bed chromatography apparatus (MBCA) having one or more zones, (b) collecting a raffinate stream or an extract stream from the first zone of the MBCA, the raffinate stream comprising the diacid and components more polar than the diacid, and the extract stream comprising the diacid and components less polar than the diacid, (c) introducing the raffinate stream or the extract stream into a second zone of the MBCA, (d) collecting a second raffinate stream or a second extract stream from the second zone of the MBCA, the raffinate stream comprising the diacid and components more polar than the diacid, and the extract stream comprising the diacid and components less polar than the diacid, (e) introducing the second raffinate stream or the second extract stream into the first zone or the second zone of the MBCA, (f) optionally repeating steps (d) and (e) until a desired degree of separation is achieved; and (g) collecting a final raffinate stream or a final extract stream from a zone the MBCA, the final raffinate stream or the extract stream comprising the diacid, thereby separating a C6- to C18-carbon diacid from the at least one impurity in the solution.

This disclosure also features method for separating a C6- to C18-carbon diacid from at least one impurity in a solution, the method comprising (a) introducing a feed stream comprising a solution comprising at least one 6- to 18-carbon diacid and at least one impurity, the at least one impurity comprising a component more polar than the diacid, a component less polar than the diacid, or both, into a first zone of a moving bed chromatography apparatus (MBCA), (b) collecting a raffinate stream or an extract stream from the MBCA, the raffinate stream comprising the diacid and components more polar than the diacid, and the extract stream comprising the diacid and components less polar than the diacid, (c) introducing the raffinate stream or the extract stream into the first zone of the MBCA, (f) optionally repeating steps (b) and (c) until a desired degree of separation is achieved; and (g) collecting a final raffinate stream or a final extract stream from the first zone of the MBCA, the final raffinate stream or the extract stream comprising the diacid, thereby separating a C6- to C18-carbon diacid from the solution.

In another aspect, this disclosure features moving bed chromatography apparatus (MBCA) for separating a C6- to C18-carbon diacid from at least one impurity in a solution, the MBCA comprising a first zone configured to receive a feed stream comprising a solution comprising at least one 6- to 18-carbon diacid and at least one impurity, the at least one impurity comprising a component more polar than the diacid, a component less polar than the diacid, or both, (b) the first zone configured to produce a raffinate stream or an extract stream from the MBCA, the raffinate stream comprising the diacid and components more polar than the diacid, and the extract stream comprising the diacid and components less polar than the diacid, (c) a second zone configured to receive the raffinate stream or the extract stream produced from the first zone, (d) the second zone configured to produce a raffinate stream or an extract stream from the MBCA, the raffinate stream comprising the diacid and components more polar than the diacid, and the extract stream comprising the diacid and components less polar than the diacid, (e) the MBCA configured to allow repeating steps (d) and (e) until a desired degree of separation is achieved to produce a final raffinate stream or a final extract stream from a zone the MBCA, the final raffinate stream or the extract stream comprising the diacid, thereby separating a C6- to C18-carbon diacid from the solution.

In some aspects, the methods and apparatus disclosed herein optionally comprising introducing the raffinate stream or the extract stream into first zone of the MBCA prior to first raffinate stream or the first extract stream introducing the raffinate stream or the extract stream into a second zone of the MBCA. In some embodiments, the MBCA comprises two or more zones, each zone comprising one or more injection points for introducing the solution; one or more injection points for introducing an eluent; a raffinate stream from which liquid can be collected; and an extract stream from which liquid can be collected.

In some embodiments, the at least one impurity is present in a final raffinate stream or a final extract stream at about 10,000 ppmw or less, about 5,000 ppmw or less, about 1,000 ppmw or less, about 500 ppmw or less, about 100 ppmw or less, about 50 ppmw or less, or about 10 ppmw or less. The at least one impurity can be a monocarboxylic acid, an alkane, or a hydroxyl acid. The at least one impurity can be more polar than the LCDA, or can be less polar than LCDA.

According to some aspects, the C6- to C18-carbon diacid recovered from the methods and apparatus disclosed herein is at least 80%, 82%, 85%, 88%, 90%, 91%, 92%, 93%, 94%, 95%, 96%, 97%, 98%, 99%, or at least 99.9% relative to the amount of the at least one impurity.

In some embodiments, the at least one 6- to 18-carbon diacid is an, or diacid, including, for example a alkane diacid or an olefin diacid. The 6- to 18-carbon diacid can be produced by chemical means or by fermentation. Thus, in some embodiments, the 6- to 18-carbon diacid is a bio-derived compound produced by fermentation.

The at least one 6- to 18-carbon diacid can be, for example, a LCDA selected from the group consisting of a C6 diacid (adipic acid), C7 diacid (pimelic acid), C8 diacid (suberic acid), C9 diacid (azelaic acid), C10 diacid (sebacic acid), C11 diacid (undecanedioic acid), C12 diacid (dodecanedioic acid), C13 diacid (tridecanedioic acid), C14 diacid (tetradecanedioic acid), C15 (pentadecanedioic acid), C16 diacid (hexadecanedioic acid), C17 diacid (heptadecanedioic acid), C18 diacid (octadecanedioic acid), and C6-18-olefin diacid.

According to some aspects, the MBCA comprises one, two or more zones. The MBCA can contain one, two, three to fifteen chromatography columns.

In some embodiments, the apparatus comprises two zones, the eluent in the first zone containing more alcohol than the eluent in the second zone, and the second zone is downstream of the first zone with respect to the flow of eluent in the system.

In some embodiments, the apparatus comprises a first zone, a second zone and a third zone, the eluent in the first zone containing more alcohol than the eluent in the second zone and the third zone and the first zone is upstream of the second and third zones with respect to the flow of eluent in the system, and the eluent in the second zone contains more alcohol than the eluent in the third zone and the second zone is upstream of the third zone with respect to the flow of eluent in the system.

In some aspects, this disclosure provides a method, means or process for obtaining a diacid comprising providing a solution comprising at least one C6- to C18-carbon diacid and at least one impurity; introducing the solution into a moving bed chromatography apparatus (MBCA) having one or more chromatography columns and at least one eluent; producing a raffinate and an extract; recovering a purified C6- to C18-carbon diacid composition from the raffinate or the extract, or both, wherein said at least one impurity is present in the purified diacid composition at about 10,000 ppmw or less, about 5,000 ppmw or less, about 1,000 ppmw or less, about 500 ppmw or less, about 100 ppmw or less, about 50 ppmw or less, or about 10 ppmw or less.

In an exemplary embodiment, the disclosure provides a method for separating adipic acid from 6-hydroxycaproic acid and caproic acid in a solution, the method comprising (a) introducing a feed stream comprising a solution comprising adipic acid, 6-hydroxycaproic acid, and caproic acid, into a first zone of moving bed chromatography apparatus (MBCA); (b) collecting a raffinate stream or an extract stream from the first zone of the MBCA, the raffinate stream comprising the adipic acid and 6-hydroxycaproic acid, and the extract stream comprising the adipic acid and caproic acid; (c) introducing the raffinate stream or the extract stream into a second zone of the MBCA; (d) collecting a second raffinate stream or a second extract stream from the second zone of the MBCA, the raffinate stream comprising the adipic acid and 6-hydroxycaproic acid, and the extract stream comprising the adipic acid and caproic acid; (e) introducing the second raffinate stream or the second extract stream into the first zone or the second zone of the MBCA; (f) optionally repeating steps (d) and (e) until a desired degree of separation is achieved; and (g) collecting a final raffinate stream or a final extract stream from a zone of the MBCA, the final raffinate stream or the extract stream comprising the adipic acid, thereby separating the adipic acid from the 6-hydroxycaproic acid and caproic acid.

In another exemplary embodiment, the disclosure provides method for separating dodecandioic acid from 12-hydroxydecanoic acid and lauric acid in a solution, the method comprising: (a) introducing a feed stream comprising a solution comprising dodecandioic acid, 12-hydroxydecanoic acid and lauric acid, into a first zone of moving bed chromatography apparatus (MBCA); (b) collecting a raffinate stream or an extract stream from the first zone of the MBCA, the raffinate stream comprising the dodecandioic acid and 12-hydroxydecanoic acid, and the extract stream comprising the dodecandioic acid and lauric acid; (c) introducing the raffinate stream or the extract stream into a second zone of the MBCA; (d) collecting a second raffinate stream or a second extract stream from the second zone of the MBCA, the raffinate stream comprising the dodecandioic acid and 12-hydroxydecanoic acid, and the extract stream comprising the dodecandioic acid and lauric acid; (e) introducing the second raffinate stream or the second extract stream into the first zone or the second zone of the MBCA; (f) optionally repeating steps (d) and (e) until a desired degree of separation is achieved; and (g) collecting a final raffinate stream or a final extract stream from a zone of the MBCA, the final raffinate stream or the extract stream comprising the dodecandioic acid, thereby separating the dodecandioic acid from the 12-hydroxydecanoic acid and lauric acid.

DEFINITIONS

While mostly familiar to those versed in the art, the following definitions are provided in the interest of clarity.

"Zone" refers to a plurality of linked chromatography columns containing, as eluent (i.e. an aqueous alcohol) and having one or more injection points for a feed mixture stream, one or more injection points for water and/or alcohol, a raffinate take-off stream from which liquid can be collected from said plurality of linked chromatography columns, and an extract take-off stream from which liquid can be collected from said plurality of linked chromatography columns. Typically, each zone has only one injection point for a feed mixture. In one aspect, each zone has only one injection point for the eluent. In another aspect, each zone has two or more injection points for water and/or alcohol.

"Raffinate" is the stream of components that move more rapidly with the liquid eluent phase compared with the solid adsorbent phase. Thus, a raffinate stream can be enriched with more polar components, and depleted of less polar components compared with a feed stream.

"Extract" is the stream of components that move more rapidly with the solid adsorbent phase compared with the liquid eluent phase. Thus, an extract stream can be enriched with less polar components, and depleted of more polar components compared with a feed stream.

"Nonadjacent" when applied to columns in the same apparatus refers to columns separated by one or more columns, for example 3 or more columns, for example 5 or more columns, or for example about 5 columns.

"LCDA" means long chain diacid(s).

"MB" means moving bed chromatography. "MBCA" means moving bed chromatography apparatus.

"SMB" means simulated moving bed chromatography.

DETAILED DESCRIPTION OF THE INVENTION

Figure 1:
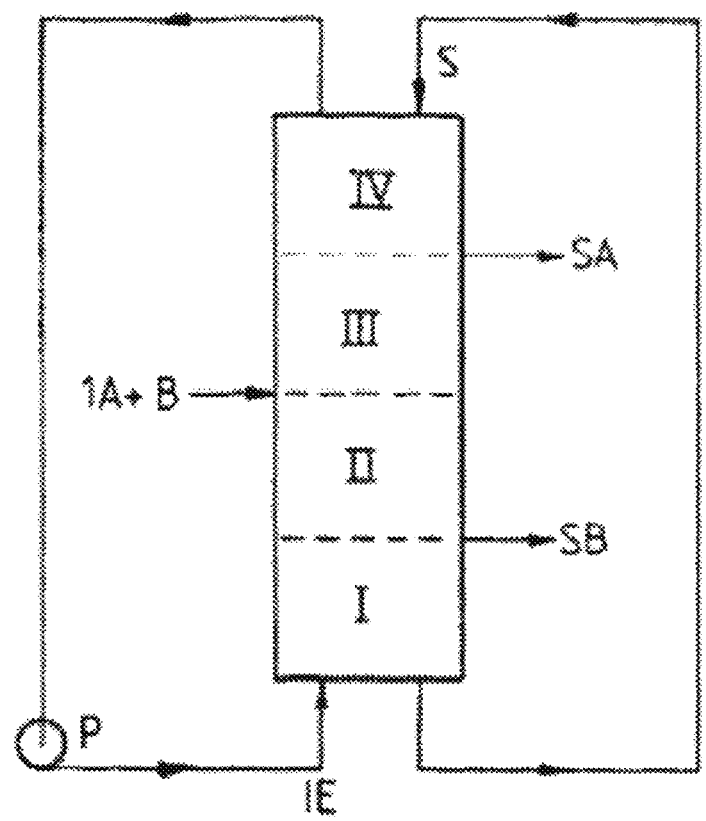
FIG. 1 illustrates the basic principles of a simulated or actual moving bed process for separating a binary mixture.

The method of the present invention comprises the separation and purification of at least one long chain diacid from other long chain diacids, monocarboxylic acids, hydroxyl acids or alkanes in a solution by simulated moving bed chromatography. The long chain diacid can comprise at least one long-chain diacid comprising an $\alpha$, $\omega$-aliphatic diacid with the main chain comprising 6 or more carbon atoms, for example, alkane diacids and olefin diacids comprising from 6 to 18 carbons. For example, the long chain diacid can be C6 diacid (adipic acid), C7 diacid (pimelic acid), C8 diacid (suberic acid), C9 diacid (azelaic acid), C10 diacid (sebacic acid), C11 diacid (undecanedioic acid), C12 diacid (dodecanedioic acid), C13 diacid (tridecanedioic acid), C14 (tetradecanedioic acid), C15 diacid (pentadecanedioic acid), C16 diacid (hexadecanedioic acid), C17 diacid (heptadecanedioic acid), C18 diacid (octadecanedioic acid), or C18-9-olefin diacid. In some aspects, the at least one long-chain diacid can be one single long-chain diacid, or a mixture of different long-chain diacids. In one aspect, the long chain diacid product can be adipic acid, sebacic acid or dodecanedioic acid. In another aspect, the long chain diacid product can be produced via chemical methods. In yet another aspect, the long chain diacid is produced by fermentation routes. In another aspect, the fermentation route comprises fermentation of long chain alkanes, fatty acids, or fatty acid esters.

In one aspect, the method of the present invention comprises introducing a feed stream comprising at least one long chain diacid in to a moving bed chromatography apparatus (MBCA). The MBCA can contain a plurality of separation zones. For example, the MBCA can contain one, two or more separation zones. In yet another aspect, the MBCA can contains 2 to 5 zones. Typically, the components separated in each zone have different polarities. Each zone contains an eluent, for example an aqueous alcohol, comprising various water:alcohol ratios, and/or a recycle stream comprising the extract and/or raffinate streams recycled back into the same zone. The eluent and/or recycle stream can be adjusted such that the long chain diacid product can be separated from different components of the feed mixture in each zone.

In another aspect, the present invention relates to compositions comprising a long chain diacid product, for example a long chain diacid product obtainable by the method of the present invention. The composition comprising a long chain diacid product comprise at least 80%, 82%, 85%, 88%, 90%, 91%, 92%, 93%, 94%, 95%, 96%, 97%, 98%, 99%, 99.5% or at least 99.9% of the long chain diacid product relative to the amount of any other long chain diacids, monocarboxylic acids, hydroxyl acids or alkanes in the composition.

Suitable feed mixtures for fractionating by the method of the present invention can be obtained by chemical and/or biological methods. Certain long-chain diacids, for example adipic acid, sebacic acid and dodecanedioic acid, can be prepared via chemical methods. For example, starting with benzene or 1,3-butadiene, dodecanedioic acid can be prepared through multiple steps of chemical reactions. Sebacic acid can be prepared through the chemical conversion of castor oil. Long-chain diacids can also be prepared via a biological method. A biological method, for example fermentation, can produce a series of long-chain diacids containing 6 through 18 carbon atoms.

The feed mixtures can contain the desired LCDA product and at least one more polar component or at least one less polar component. The less polar components can have a stronger adherence to the adsorbent used in the method of the present invention as compared to the desired LCDA product. During operation, such less polar components typically move with the solid adsorbent phase in preference to the liquid eluent phase. The more polar components have a weaker adherence to the adsorbent used in the method of the present invention than does the LCDA product. During operation, such more polar components typically move with the liquid eluent phase in preference to the solid adsorbent phase. In general, more polar components will be separated into a raffinate stream, and less polar components will be separated into an extract stream.

Examples of the more and less polar components include (1) other compounds from the manufacturing process (for example, other unwanted LCDAs, hydroxylated fatty acids, fatty acids, fatty acid esters, hydrocarbons, or hydroxycarboxylic acids), (2) byproducts formed during storage, refining and previous concentration steps and (3) contaminants from solvents or reagents which are utilized during previous concentration or purification steps.

In one aspect, the feed mixture is a LCDA containing mainly the desired LCDA.

In one aspect, the feed mixture is an aqueous mixture containing the LCDA, such as a fermentation broth from a biological fermentation.

MBCAs suitable for the separation and purifying a LCDA from a feed mixture may comprise one or more separation zones. For example, a MBCA may comprise only one zone to separate a desired product component from other impurities when all of those impurities elute either faster or slower than the desired product component. Further as an example, a MBCA may comprise more than one separation zone, and the components separated in each zone may have different polarities, or different affinities for a particular stationary phase or particular eluent.

In one aspect, the MBCA is an SMB apparatus. SMB apparatuses suitable for the separation and purifying a LCDA from a feed mixture may comprise one or more separation zones. For example, a SMB may comprise only one zone to separate a desired product component from other impurities when all of those impurities elute either faster or slower than the desired product component. Further as an example, a SMB apparatus may comprise more than one separation zone, and the components separated in each zone may have different polarities, or different affinities for a particular stationary phase or particular eluent.

In one aspect, the method of the invention comprises a plurality of zones in a chromatography apparatus, for example, two or more zones can be used. In another aspect of the present invention there can be 2 to 5 zones. Typically, the components separated in each zone of the apparatus used in the method of the present invention have different polarities. The eluent, such aqueous alcohol, containing mixture present in each zone has a different water:alcohol ratio; and/or the rate at which liquid collected via the extract and raffinate streams in each zone is recycled back into the same zone is adjusted such that the LCDA product can be separated from different components of the feed mixture in each zone.

When the apparatus used in the method of the present invention has two zones, the present invention typically provides a chromatographic separation method for recovering a LCDA product, from a feed mixture, which method comprises introducing the feed mixture to a simulated or actual moving bed chromatography apparatus having a plurality of linked chromatography columns containing, as eluent, an aqueous alcohol, wherein the apparatus has a first zone and a second zone, each zone having an extract stream and a raffinate stream from which liquid can be collected from said plurality of linked chromatography columns, and wherein (a) a raffinate stream containing the LCDA product together with more polar components is collected from a column in the first zone and introduced to a nonadjacent column in the second zone, and/or (b) an extract stream containing the LCDA product together with less polar components is collected from a column in the second zone and introduced to a nonadjacent column in the first zone, said LCDA product being separated from less polar components of the feed mixture in the first zone, and said LCDA product being separated from more polar components of the feed mixture in the second zone.

In an aspect of the present invention, when the apparatus used in the method contains two zones, the eluent in the first zone contains more alcohol than the eluent in the second zone, and the second zone is downstream of the first zone with respect to the flow of eluent in the system. Thus, the eluent in the system typically moves from the first zone to the second zone. Conversely, the solid adsorbent phase typically moves from the second zone to the first zone. Typically, the two zones do not overlap, i.e. there are no chromatographic columns which are in both zones.

In a further aspect of the invention, the apparatus has a first zone, a second zone and a third zone. If the eluent is aqueous alcohol, the water:alcohol ratios of the aqueous alcohol eluent present in the first, second and third zones are typically different. As will be evident to one skilled in the art, this has the consequence that impurities having different polarities can be removed in each zone.

When the apparatus has three zones, the eluent in the first zone can contain more alcohol than the eluent in the second zone and the third zone and the first zone is upstream of the second and third zones with respect to the flow of eluent in the system. Typically, the eluent in the second zone contains more alcohol than the eluent in the third zone and the second zone is upstream of the third zone with respect to the flow of eluent in the system. Typically, in the first zone, said LCDA product is separated from components of the feed mixture which are less polar than the LCDA product. Typically, in the second zone, said LCDA product is separated from components of the feed mixture which are less polar than the LCDA product but more polar than the components separated in the first zone. Typically, in the third zone, said LCDA product is separated from components of the feed mixture which are more polar than the LCDA product.

Any known simulated or actual moving bed chromatography apparatus may be utilized for the purposes of the method of the present invention, as long as the apparatus is configured with the multiple, in particular two, zones which characterize the method of the present invention. Those apparatuses described in U.S. Pat. No. 2,985,589, U.S. Pat. No. 3,696,107, U.S. Pat. No. 3,706,812, U.S. Pat. No. 3,761,533, FR-A-2103302, FR-A-2651148, FR-A-2651149, U.S. Pat. No. 6,979,402, U.S. Pat. No. 5,069,883 and U.S. Pat. No. 4,764,276 may all be used if configured in accordance with the method of the present invention.

The number of columns can be 8 or more, for example 15 or more. In one aspect of the present invention, 15 or 16 columns can be used. In another aspect, 19 or 20 columns can be used. In other aspects, 30 or more columns can be used.

Each zone can consist of an approximately equal share of the total number of columns. For example, in the case of an apparatus configured with two zones, each zone typically consists of approximately half of the total number of chromatographic columns in the system. The first zone can comprise 4 or more, for example 8 or more, or about 8 columns. The second zone can comprise 4 or more, for example 7 or more, or about 7 or 8 columns.

The dimensions of the columns used in the apparatus will depend on the volume of feed mixture to be purified. The diameter of each column can be between 10 mm and 5 m, for example between 5 mm and 500 mm, between 25 and 250 mm, between 50 and 100 mm, between 70 and 80 mm, between 0.5 m and 5 m, between 1 m and 4 m, or between 2 m and 4 m. The length (i.e., height) of each column can be between 10 cm and 5 m, for example between 10 and 200 cm, between 25 and 150 cm, between 70 and 110 cm, between 80 and 100 cm, between 0.5 and 5 m, between 1 m and 4 m, between 2 m and 4 m, or between 3 m and 4 m.

The columns in each zone can have identical dimensions but may, for certain applications, have different dimensions.

The flow rates to the column are limited by maximum pressures across the series of columns and will depend on the column dimensions and particle size of the solid phases. Larger diameter columns will in general need higher flows to maintain linear flow through the columns.

For the typical column sizes outlined above, and for an apparatus having two zones, the flow rate of eluent into the first zone can be from 1 to 3,000 L/min, for example from 1 to 4.5 L/min, from 1.5 to 2.5 L/min, from 100 to 2,000 L/min, from 200 to 1,500 L/min, or from 200 to 1,200 L/min. The flow rate of the extract from the first zone can be from 0.1 to 1,000 L/min, for example from 0.1 to 2.5 L/min, from 0.5 to 2.25 L/min, from 100 to 1,000 L/min, from 200 to 1,000 L/min, from 100 to 400 L/min, or from 700 to 1,000 L/min. In aspects of the present invention where part of the extract from the first zone can be recycled back into the first zone, the flow rate of recycle can be for example from 0.7 to 600 L/min, from 200 to 600 L/min, from 0.7 to 1.4 L/min, for example about 1 L/min, about 375 L/min, about 80 L/min, or about 320 L/min. The flow rate of the raffinate from the first zone can be from 0.2 to 3,000 L/min, for example from 0.2 to 2.5 L/min, from 0.3 to 2.0 L/min, from 100 to 3,000 L/min, from 200 to 3,000 L/min, from 400 to 2,800 L/min, from 300 to 800 L/min, from 2,000 to 3,000 L/min. In aspects where part of the raffinate from the first zone can be recycled back into the first zone, the flow rate of recycle can be for example from 0.3 to 1,200 L/min, from 100 to 1,200 L/min, from 0.3 to 1.0 L/min, for example about 0.5 L/min, about 400 L/min, about 70 L/min, or about 350 L/min. The flow rate of introduction of the feed mixture into the first zone can be from 5 mL/min to 3,000 L/min, for example from 5 to 150 mL/min, from 10 to 100 mL/min, from 20 to 60 mL/min, from 100 to 3,000 L/min, from 200 to 2500 L/min, or from 400 to 2500 L/min.

For the typical column sizes outlined above, and for an apparatus having two zones, the flow rate of eluent into the second zone can be from 1 to 2,500 L/min, for example from 1 to 4 L/min, from 1.5 to 3.5 L/min, from 100 to 2,000 L/min, from 200 to 1,500 L/min, or from 200 to 1,200 L/min. The flow rate of the extract from the second zone can be from 0.5 to 900 L/min, for example from 0.5 to 2 L/min, from 0.7 to 1.9 L/min, from 120 to 900 L/min, from 200 to 800 L/min, from 100 to 400 L/min, or from 700 to 1,000 L/min. In aspects where part of the extract from the second zone is recycled back into the second zone, the flow rate of recycle can be for example from 0.6 to 600 L/min, from 200 to 600 L/min, from 0.6 to 1.4 L/min, for example from 0.7 to 1.1 L/min, about 0.9 L/min, about 340 L/min, about 70 L/min, or about 290 L/min. The flow rate of the raffinate from the second zone can be from 0.5 to 3,000 L/min, for example from 0.5 to 2.5 L/min, from 0.7 to 1.8 L/min, about 1.4 L/min, from 100 to 3,000 L/min, from 200 to 3,000 L/min, from 400 to 2,800 L/min, from 300 to 800 L/min, from 2,000 to 3,000 L/min.

References to rates at which liquid is collected or removed via the various extract and raffinate streams refer to volumes of liquid removed in an amount of time, typically L/minute. Similarly, references to rates at which liquid is recycled back into the same zone, typically to an adjacent column in the same zone, refer to volumes of liquid recycled in an amount of time, typically L/minute.

Part of one or more of the extract stream from the first zone, the raffinate stream from the first zone, the extract stream from the second zone, and the raffinate stream from the second zone can be recycled back into the same zone, for example into an adjacent column in the same zone.

This recycle is different from the feeding of an extract or raffinate stream into a non-adjacent column in another zone. Rather, the recycle involves feeding part of the extract or raffinate stream out of a zone back into the same zone, for example into an adjacent column in the same zone.

Figure 9:
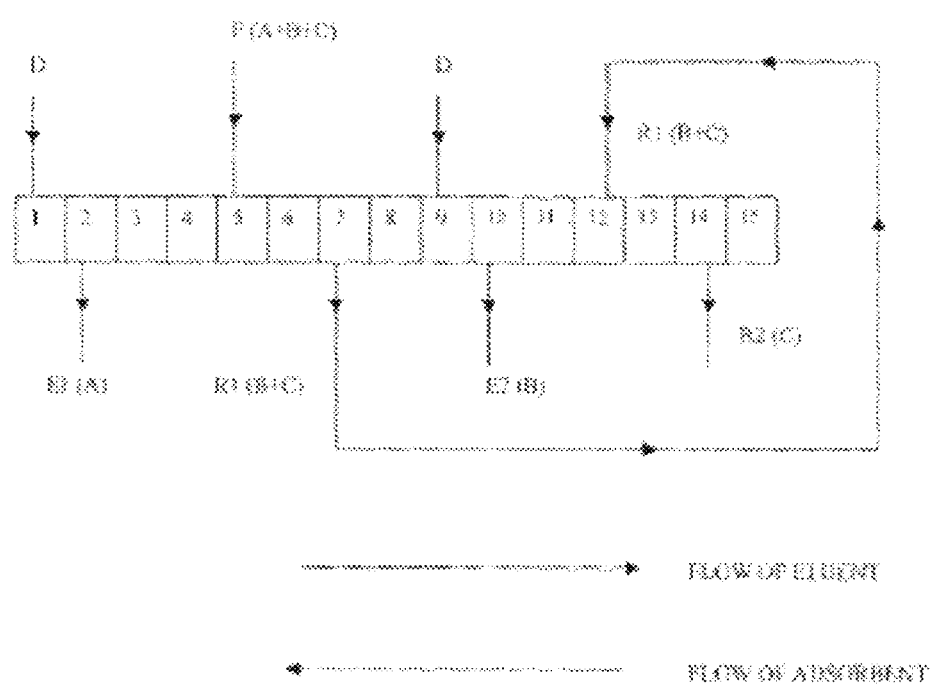
FIG. 9 illustrates an alternative method for an aspect of the invention for purifying desired LCDA from faster and slower running components (i.e. more polar and less polar impurities).
Figure 10:
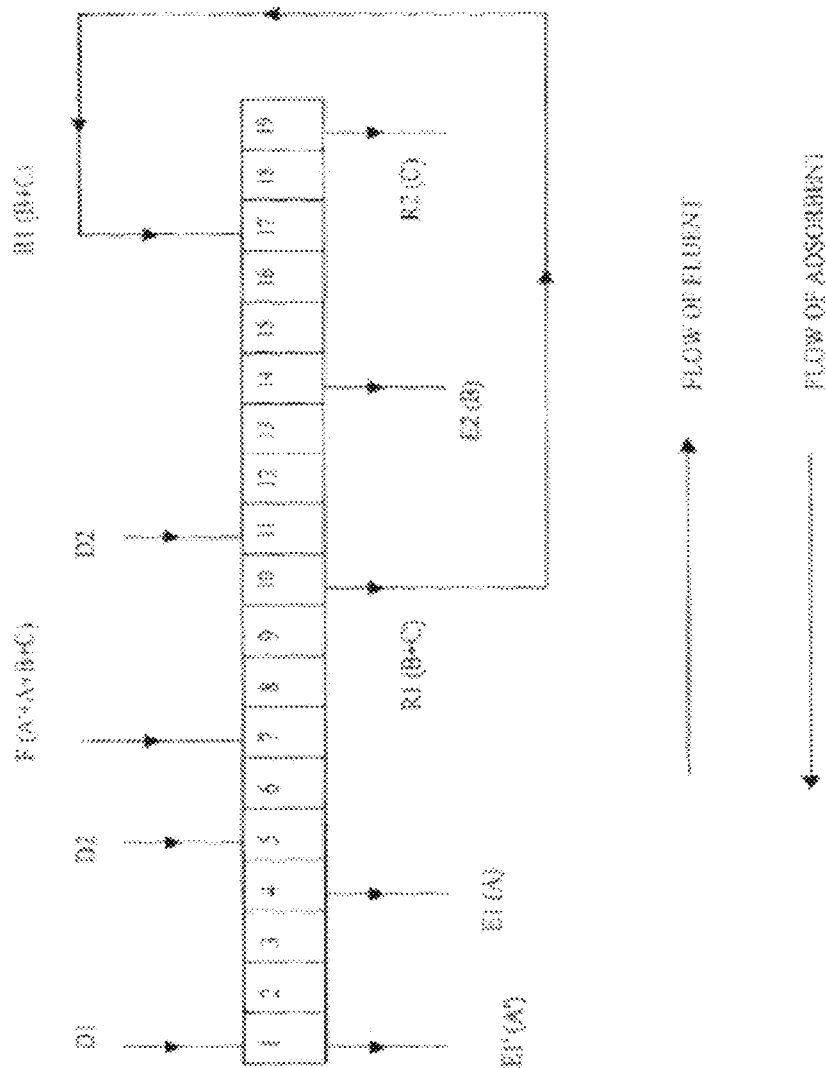
FIG. 10 illustrates an aspect of the invention for purifying desired LCDA from faster and slower running components (i.e. more polar and less polar impurities).

The rate at which liquid collected via the extract or raffinate stream from the first or second zones is recycled back into the same zone cam be the rate at which liquid collected via that stream is fed back into the same zone, for example into an adjacent column in the same zone. This can be seen with reference to FIG. 9. The rate of recycle of extract in the first zone is the rate at which extract collected from the bottom of column 2 is fed into the top of column 3, i.e. the flow rate of liquid into the top of column 3. The rate of recycle of extract in the second zone is the rate at which extract collected at the bottom of column 10 is fed into the top of column 11, i.e. the flow rate of liquid into the top of column 11.

Recycle of the extract and/or raffinate streams can be effected by feeding the liquid collected via that stream into a container, and then pumping an amount of that liquid from the container back into the same zone. In this case, the rate of recycle of liquid collected via a particular extract or raffinate stream, for example back into an adjacent column in the same zone, is the rate at which liquid is pumped out of the container back into the same zone, for example into an adjacent column.

The amount of liquid being introduced into a zone via the eluent and feedstock streams is balanced with the amount of liquid removed from a zone, and recycled back into the same zone. Thus, with reference to FIG. 9, for the extract stream, the flow rate of eluent (desorbent) into the first or second zone (D) is equal to the rate at which liquid collected via the extract stream from that zone accumulates in a container (E1/E2) added to the rate at which extract is recycled back into the same zone (D-E1/D-E2). For the raffinate stream in a zone, the rate at which extract is recycled back into a zone (D-E1/D-E2) added to the rate at which feedstock is introduced into a zone (F/R1) is equal to the rate at which liquid collected via the raffinate stream from that zone accumulates in a container (R1/R2) added to the rate at which raffinate is recycled back into the same zone (D+F-E1-R1/D+R1-E2-R2).

The rate at which liquid collected from a particular extract or raffinate stream from a zone accumulates in a container can also be thought of as the net rate of removal of that extract or raffinate stream from that zone.

The rate at which liquid collected via the extract stream out of the first zone is recycled back into the first zone can differ from the rate at which liquid collected via the extract stream out of the second zone is recycled back into the second zone, and/or the rate at which liquid collected via the raffinate stream out of the first zone is recycled back into the first zone can differ from the rate at which liquid collected via the raffinate stream out of the second zone is recycled back into the second zone.

Varying the rate at which liquid collected via the extract and/or raffinate streams in each zone is recycled back into the same zone has the effect of varying the amount of more polar and less polar components present in the other extract and raffinate streams. Thus, for example, a lower extract recycle rate results in fewer of the less polar components in that zone being carried through to the raffinate stream in that zone. A higher extract recycle rate results in more of the less polar components in that zone being carried through to the raffinate stream in that zone. This can be seen, for example, in the specific aspect of the invention shown in FIG. 6. The rate at which liquid collected via the extract stream in the first zone is recycled back into the same zone (D-E1) will affect to what extent any of component A is carried through to the raffinate stream in the first zone (R1).

The rate at which liquid collected via the extract stream from the first zone is recycled back into the first zone can be faster than the rate at which liquid collected via the extract stream from the second zone is recycled back into the second zone. In an aspect of the present invention, a raffinate stream containing the LCDA product together with more polar components is collected from a column in the first zone and introduced to a nonadjacent column in the second zone, and the rate at which liquid collected via the extract stream from the first zone is recycled back into the first zone can be faster than the rate at which liquid collected via the extract stream from the second zone is recycled back into the second zone.

Alternatively, the rate at which liquid collected via the extract stream from the first zone is recycled back into the first zone can be slower than the rate at which liquid collected via the extract stream from the second zone is recycled back into the second zone.

The rate at which liquid collected via the raffinate stream from the second zone is recycled back into the second zone can be faster than the rate at which liquid collected via the raffinate stream from the first zone is recycled back into the first zone. In an aspect of the present invention, an extract stream containing the LCDA product together with less polar components can be collected from a column in the second zone and introduced to a nonadjacent column in the first zone, and the rate at which liquid collected via the raffinate stream from the second zone is recycled back into the second zone can be faster than the rate at which liquid collected via the raffinate stream from the first zone is recycled back into the first zone.

Alternatively, the rate at which liquid collected via the raffinate stream from the second zone is recycled back into the second zone can be slower than the rate at which liquid collected via the raffinate stream from the first zone is recycled back into the first zone.

The step time, i.e. the time between shifting the points of injection of the feed mixture and eluent, and the various take off points of the collected fractions depends on the number and dimensions of the columns used, and the flow rate through the apparatus. The step time can be from 100 to 1200 seconds, for example from 100 to 1000 seconds, from 200 to 800 or from about 250 to about 750 seconds. In some aspects of the present invention, the step time can be from 100 to 400 seconds, or from 200 to 300 seconds, or about 250 seconds. In other aspects, the step time can be from 600 to 900 seconds, or from 700 to 800 seconds, or about 750 seconds. In other aspects, the step time can be from 400 to about 800 seconds, from about 500 to 700 seconds, or about 600 seconds.

In one aspect of the method of the present invention, actual moving bed chromatography is used.

Conventional adsorbents for actual and simulated moving bed systems can be used in the method of the present invention. In some aspects, the stationary phase comprises at least one material selected from the group consisting of adsorption resin, activated carbon, floridin, diatomite and silica gel. In some aspects, the stationary phase is Orpheus non-polar silica-based stationary phase adsorbent (available from Orochem Technologies Inc., Naperville, Ill., USA). In some aspects, the stationary phase is C8, C18, or Polar C18 adsorbent (available from Orochem Technologies Inc., Naperville, Ill., USA).

In some aspects of the present invention, the adsorption resin can be chosen from macroporous adsorption resins. In other aspects, the macroporous adsorption resin can be chosen from nonpolar macroporous adsorption resins for example DOW XAD 418. In yet other aspects, the macroporous adsorption resin can be chosen from polar macroporous adsorption resins. In some aspects, the stationary phase comprises adsorption resin and at least one material chosen from activated carbon, floridin, diatomite and silica gel.

Each chromatographic column can contain the same or a different adsorbent. Typically, each column contains the same adsorbent. Examples of such commonly used materials are polymeric beads, ion exchange resins, adsorption resin, activated carbon, floridin, diatomite and silica gel. In one aspect, the adsorbent used in the method of the present invention is non-polar.

The shape of the adsorbent stationary phase material can be, for example, spherical or nonspherical beads. In an aspect of the present invention, the stationary phase material can be substantially spherical beads. Such beads can have a diameter of from 40 to 500 microns, for example from 100 to 500 microns, from 250 to 500 microns, from 250 to 400 microns, or from 250 to 350 microns. Particle sizes can be somewhat larger than particle sizes of beads used in the past in simulated and actual moving bed processes. Use of larger particles enables a lower pressure of eluent to be used in the system. This, in turn, has advantages in terms of cost savings, efficiency and lifetime of the apparatus.

The adsorbent can have a pore size of from 6 to 50 nm, for example from 15 to 45 from 20 to 40 nm, from 25 to 35 nm, from 6 to 20 nm, from 7 to 12 nm, or from 8 to 11 nm.

The eluent used in the method of the present invention is not in a supercritical state. Typically, the eluent is a liquid. The eluent can be an aqueous alcohol. The aqueous alcohol can comprise water and one or more short chain alcohols. The short chain alcohol can have from 1 to 6 carbon atoms. Examples of suitable alcohols include methanol, ethanol, n-propanol, i-propanol, n-butanol, i-butanol, s-butanol and t-butanol. In some aspects of the present invention, methanol and ethanol can be used. In another aspect, methanol can be used.

The average water:alcohol ratio of the eluent in the entire apparatus can be from 0.1:99.9 to 95:5 parts by volume, for example from 0.1:99.9 to 9:91 parts by volume, from 0.25:99.75 to 7:93 parts by volume, from 0.5:99.5 to 6:94 parts by volume, from 5:95 to 20:80 by volume, from 50:50 to 95:5 parts by volume, from 30:70 to 70:30 parts by volume, or from 30:70 to 50:50 parts by volume.

The eluting power of the eluent in each of the zones can be different. In an aspect of the present invention, the eluting power of the eluent in the first zone can be greater than that of the eluent in the second and subsequent zones. In practice this can be achieved by varying the relative amounts of water and alcohol in each zone. Alcohols are generally more powerful desorbers than water. Thus, the amount of alcohol in the eluent in the first zone can be greater than the amount of alcohol in the eluent of the second and subsequent zones.

In aspects of the present invention where the aqueous alcohol present in each zone has a different water alcohol content, the water:alcohol ratio of the eluent in the first zone can be from 0:100 to 5:95 parts by volume, for example from 0.1:99.9 to 2.5:97.5 parts by volume, from 0.25:99.75 to 2:98 parts by volume, or from 0.5:99.5 to 1.5:98.5 parts by volume. In these aspects, the water:alcohol ratio of the eluent in the second zone can be from 3:97 to 7:93 parts by volume, from 4:96 to 6:94 parts by volume, or from 4.5:95.5 to 5.5:94.5 parts by volume.

In an aspect of the present invention where the aqueous alcohol present in each zone has a different water alcohol content, the water:alcohol ratio of the eluent in the first zone can be from 0.5:99.5 to 1.5:98.5 parts by volume, and the water:alcohol ratio of the eluent in the second zone can be from 4.5:95.5 to 5.5:94.5 parts by volume.

In aspects of the present invention where the rate at which liquid collected via the extract and raffinate streams in each zone is recycled back into the same zone is adjusted such that the LCDA product can be separated from different components of the feed mixture in each zone, the water:alcohol ratio of the eluents in each zone can be the same or different. The water:alcohol ratio of the eluent in each zone can be from 0.5:99.5 to 5.5:94.5 parts by volume. In one aspect, the water:alcohol ratio of the eluent in the first zone can be lower than the water:alcohol ratio of the eluent in the second zone. In another aspect, the water:alcohol ratio of the eluent in the first zone can be higher than the water:alcohol ratio of the eluent in the second zone. In a further aspect, the water:alcohol ratio of the eluent in the first zone can be the same as the water:alcohol ratio of the eluent in the second zone.

The ratios of water and alcohol in each zone referred to above are average ratios within the totality of the zone.

The water:alcohol ratio of the eluent in each zone can be controlled by introducing water and/or alcohol into one or more columns in the zones. Thus, for example, to achieve a lower water:alcohol ratio in the first zone than in the second zone, water can be introduced more slowly into the first zone than the second zone. In some aspects of the present invention, essentially pure alcohol and essentially pure water can be introduced at different points in each zone. The relative flow rates of these two streams will determine the overall solvent profile across the zone. In other aspects, different alcohol/water mixtures can be introduced at different points in each zone. That will involve introducing two or more different alcohol/water mixtures into the zone, each alcohol/water mixture having a different alcohol:water ratio. The relative flow rates and relative concentrations of the alcohol/water mixtures in this aspect will determine the overall solvent profile across the zone. In other aspects, where the water:alcohol ratio of the eluent in each zone is the same, the same alcohol/water mixture is introduced to each zone.

The method of the present invention can be conducted at from 15 to 60° C., for example at from 20 to 40° C., or at about 30° C. Thus, the method can be carried out at room temperature, but can be conducted at elevated temperatures.

The method of the present invention involves introducing a feed stream into one zone (for example the first zone), collecting a first intermediate stream enriched with the LCDA product and introducing the first intermediate stream into another zone (for example the second zone). Thus, when the apparatus has two zones, the method involves either (a) collecting a first intermediate stream from the first zone and introducing it into the second zone, or (b) collecting a first intermediate stream from the second zone and introducing it into the first zone. In this way, the LCDA product can be separated from both more and less polar components in a single method.

Either (a) a raffinate stream containing the LCDA product together with more polar components can be collected from a column in the first zone and introduced to a nonadjacent column in the second zone, or (b) an extract stream containing the LCDA product together with less polar components can be collected from a column in the second zone and introduced to a nonadjacent column in the first zone.

In one aspect of the present invention, the apparatus has two zones, and the method comprises: (i) introducing the feed mixture into the first zone, and removing a first raffinate stream enriched with the LCDA product and a first extract stream depleted of the LCDA product, and (ii) introducing the first raffinate stream into the second zone, removing a second raffinate stream depleted of the LCDA product, and collecting a second extract stream to obtain the LCDA product.

Figure 2:
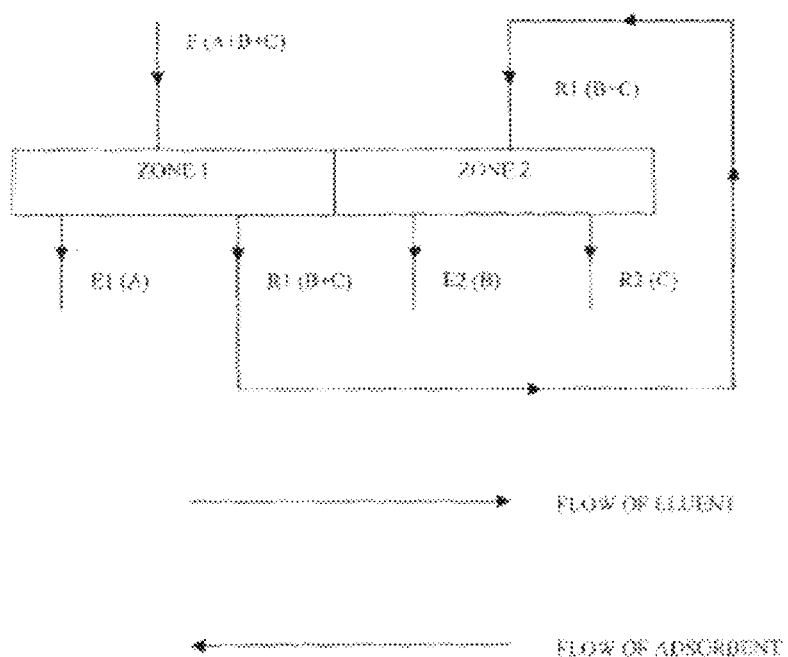
FIG. 2 illustrates a first aspect of the invention which is suitable for separating desired LCDA from faster and slower running components (i.e. more polar and less polar impurities).

This aspect is illustrated in FIG. 2. A feed mixture F comprising the LCDA product (B) and more polar (C) and less polar (A) components is introduced into the first zone. In the first zone, the less polar components (A) are removed as extract stream E1. The LCDA product (B) and more polar components (C) are removed as raffinate stream R1. Raffinate stream R1 is then introduced into the second zone. In the second zone, the more polar components (C) are removed as raffinate stream R2. The LCDA product (B) is collected as extract stream E2.

Figure 4:
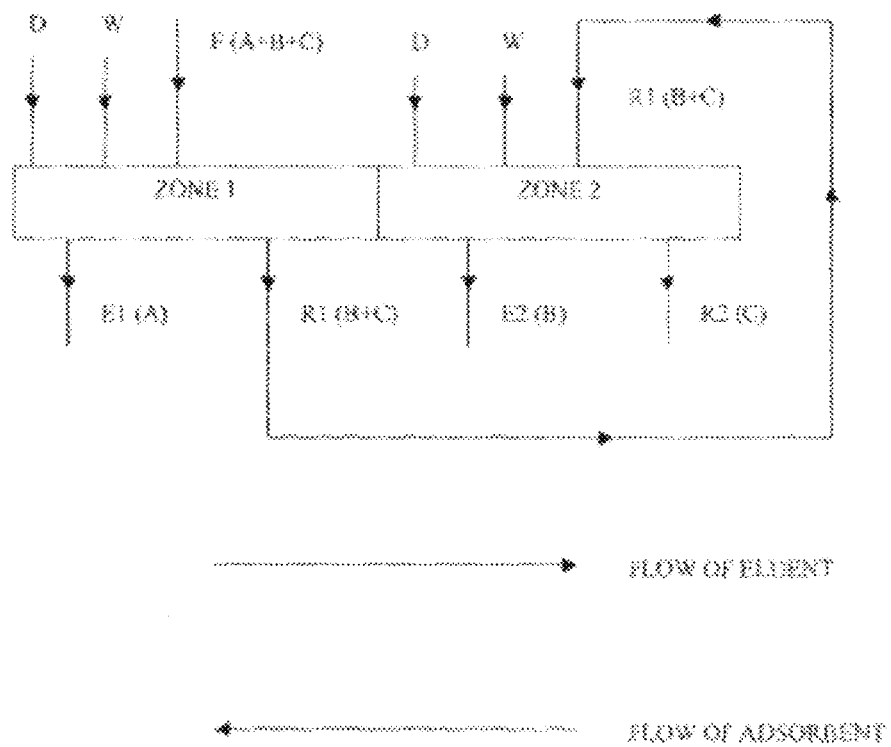
FIG. 4 illustrates in more detail the first aspect of the invention which is suitable for separating desired LCDA from faster and slower running components (i.e. more polar and less polar impurities).

This aspect is illustrated in more detail in FIG. 4 and FIG. 4 is identical to FIG. 2, except that the points of introduction of the alcohol desorbent (D) and water (W) into each zone are shown. The alcohol desorbent (D) and water (W) together make up the eluent. The (D) phase can be essentially pure alcohol, but may, in certain aspects be an alcohol/water mixture comprising mainly alcohol. The (W) phase can be essentially pure water, but may, in certain aspects be an alcohol/water mixture comprising mainly water, for example a 98% water/2% methanol mixture.

Figure 6:
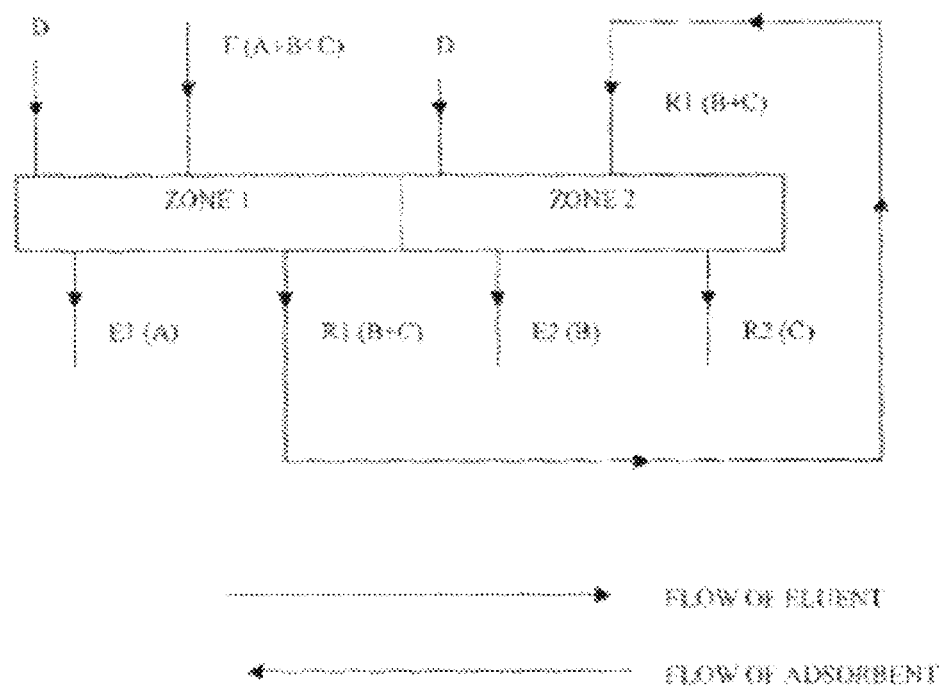
FIG. 6 illustrates in more detail an alternative method for the first aspect of the invention which is suitable for separating desired LCDA from faster and slower running components (i.e. more polar and less polar impurities).

A further illustration of this aspect is shown in FIG. 6. Here there is no separate water injection point, and instead an aqueous alcohol desorbent is injected at (D).

The separation into raffinate and extract stream can be aided by varying the desorbing power of the eluent within each zone. This can be achieved by introducing the alcohol (or alcohol rich) component of the eluent and the water (or water rich) component at different points in each zone. Thus, typically, the alcohol is introduced upstream of the extract take-off point and the water is introduced between the extract take-off point and the point of introduction of the feed into the zone, relative to the flow of eluent in the system. This is shown in FIG. 4.

Alternatively, the separation can be aided by varying the rates at which liquid collected via the extract and raffinate streams from the two zones is recycled back into the same zone.

Typically, in this aspect, the rate at which liquid collected via the extract stream from the first zone is recycled back into the first zone is faster than the rate at which liquid collected via the extract stream from the second zone is recycled back into the second zone; or the water:alcohol ratio of the eluent in the first zone is lower than that in the second zone.

In this aspect the first raffinate stream in the first zone can be removed downstream of the point of introduction of the feed mixture into the first zone, with respect to the flow of eluent in the first zone.

In this aspect, the first extract stream in the first zone can be removed upstream of the point of introduction of the feed mixture into the first zone, with respect to the flow of eluent in the first zone.

In this aspect, the second raffinate stream in the second zone can be removed downstream of the point of introduction of the first raffinate stream into the second zone, with respect to the flow of eluent in the second zone.

In this aspect, the second extract stream in the second zone can be collected upstream of the point of introduction of the first raffinate stream into the second zone, with respect to the flow of eluent in the second zone.

In this aspect, the alcohol or aqueous alcohol can be introduced into the first zone upstream of the point of removal of the first extract stream, with respect to the flow of eluent in the first zone.

In this aspect, when water is introduced into the first zone, the water can be introduced into the first zone upstream of the point of introduction of the feed mixture but downstream of the point of removal of the first extract stream, with respect to the flow of eluent in the first zone.

In this aspect, the alcohol or aqueous alcohol can be introduced into the second zone upstream of the point of removal of the second extract stream, with respect to the flow of eluent in the second zone.

In this aspect, when water is introduced into the second zone, the water can be introduced into the second zone upstream of the point of introduction of the first raffinate stream but downstream of the point of removal of the second extract stream, with respect to the flow of eluent in the second zone.

In a second aspect of the present invention, the apparatus has two zones, and the method comprises: (i) introducing the feed mixture into the second zone, and removing a first raffinate stream depleted of the LCDA product and a first extract stream enriched in the LCDA product, and (ii) introducing the first extract stream into the first zone, removing a second extract stream depleted of the LCDA product, and collecting a second raffinate stream to obtain the LCDA product.

Figure 3:
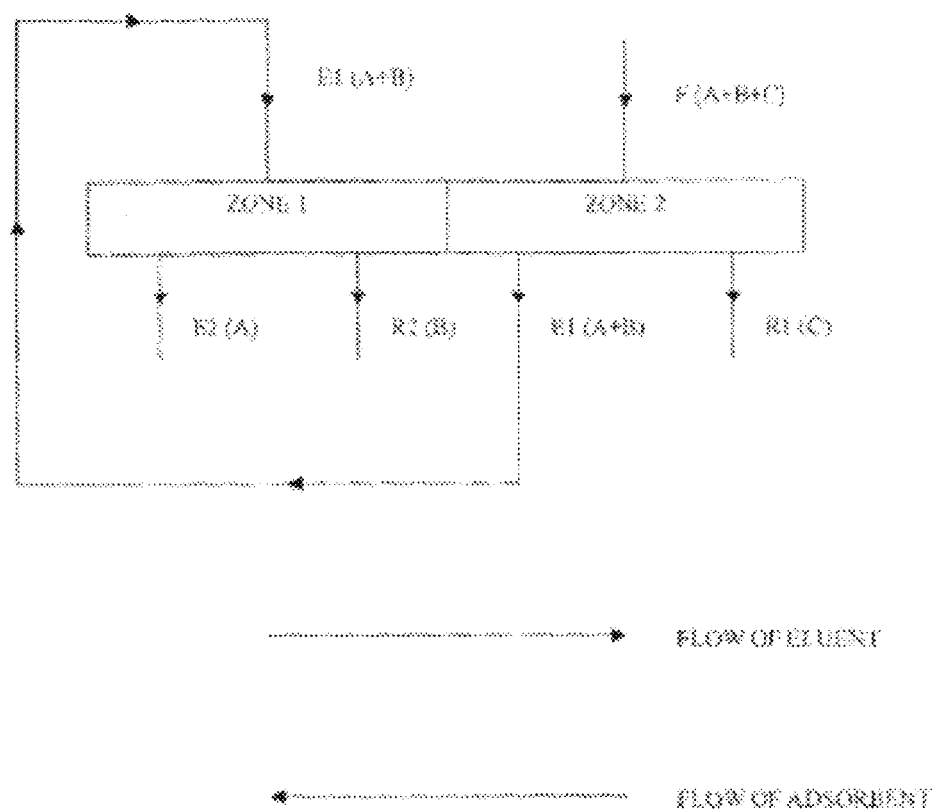
FIG. 3 illustrates a second aspect of the invention which is suitable for separating desired LCDA from faster and slower running components (i.e. more polar and less polar impurities).

This second aspect is illustrated in FIG. 3. A feed mixture F comprising the LCDA product (B) and more polar (C) and less polar (A) components is introduced into the second zone. In the second zone, the more polar components (C) are removed as raffinate stream R1. The LCDA product (B) and less polar components (A) are collected as extract stream E1. Extract stream E1 is then introduced to the first zone. In the first zone, the less polar components (A) are removed as extract stream E2. The LCDA product (B) is collected as raffinate stream R2.

Figure 5:
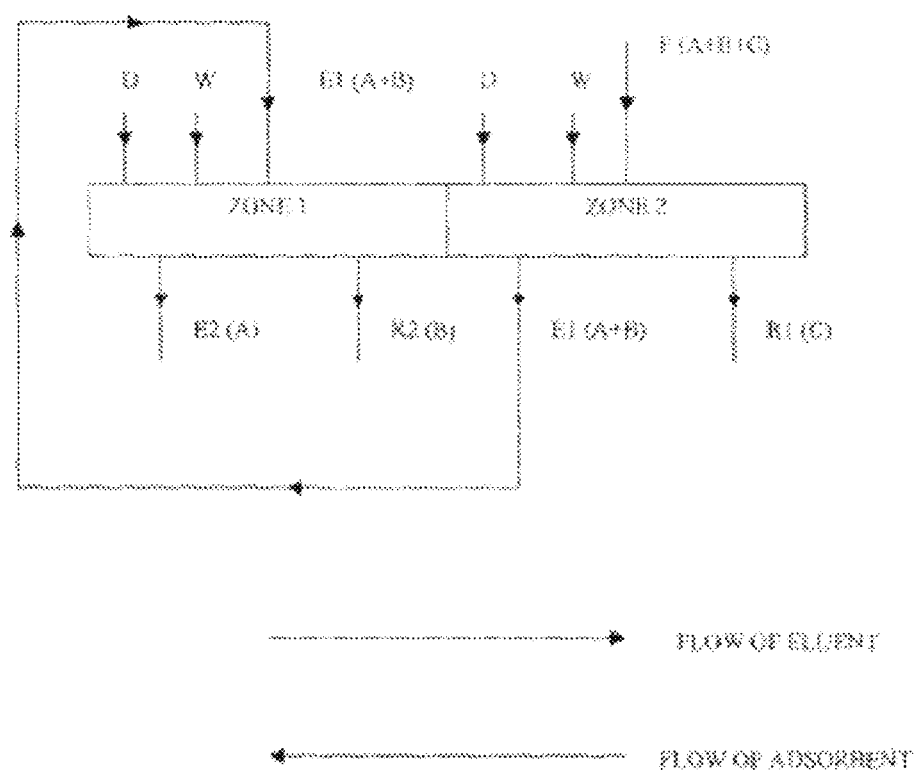
FIG. 5 illustrates in more detail the second aspect of the invention which is suitable for separating desired LCDA from faster and slower running components (i.e. more polar and less polar impurities).

This second aspect is illustrated in more detail in FIG. 5 and FIG. 5 is identical to FIG. 3, except that the points of introduction of the short chain alcohol desorbent (D) and water (W) into each zone are shown. As above, the (D) phase can be essentially pure alcohol, but may, in certain aspects be an alcohol/water mixture comprising mainly alcohol. The (W) phase can be essentially pure water, but may, in certain aspects be an alcohol/water mixture comprising mainly water, for example a 98% water/2% methanol mixture.

Figure 7:
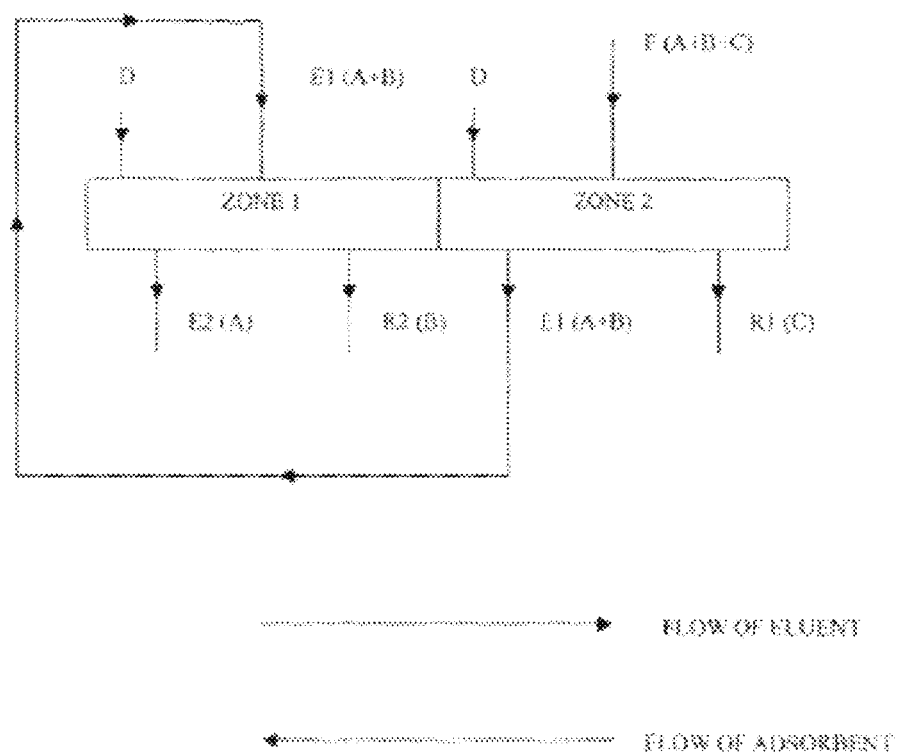
FIG. 7 illustrates in more detail an alternative method for the second aspect of the invention which is suitable for separating desired LCDA from faster and slower running components (i.e. more polar and less polar impurities).
Figure 8:
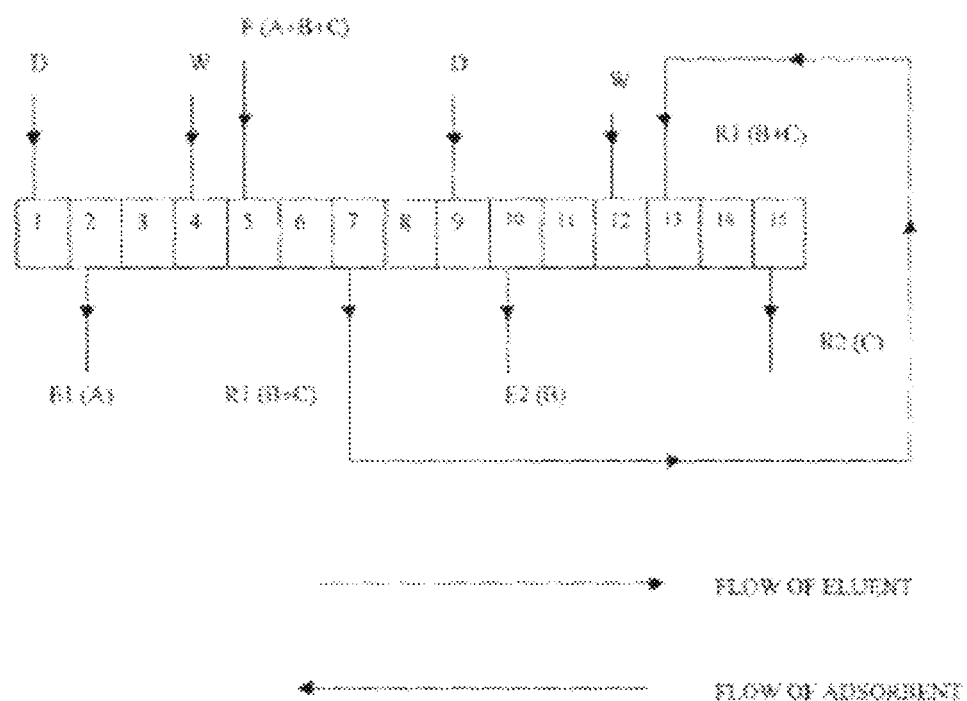
FIG. 8 illustrates an aspect of the invention for purifying desired LCDA from faster and slower running components (i.e. more polar and less polar impurities).

A further illustration of this second aspect is shown in FIG. 7. Here there is no separate water injection point, and instead an aqueous alcohol desorbent is injected at (D).

In this second aspect, the rate at which liquid collected via the raffinate stream from the second zone is reintroduced into the second zone can be faster than the rate at which liquid collected via the raffinate stream from the first zone is reintroduced into the first zone; or the water:alcohol ratio of the eluent in the first zone can be lower than that in the second zone.

In this second aspect, the first raffinate stream in the second zone can be removed downstream of the point of introduction of the feed mixture into the second zone, with respect to the flow of eluent in the second zone.

In this second aspect, the first extract stream in the second zone can be collected upstream of the point of introduction of the feed mixture into the second zone, with respect to the flow of eluent in the second zone.

In this second aspect, the second raffinate stream in the first zone can be collected downstream of the point of introduction of the first extract stream into the first zone, with respect to the flow of eluent in the first zone.

In this second aspect, the second extract stream in the first zone can be removed upstream of the point of introduction of the first extract stream into the first zone, with respect to the flow of eluent in the first zone.

In this second aspect, the alcohol or aqueous alcohol can be introduced into the second zone upstream of the point of removal of the first extract stream, with respect to the flow of eluent in the second zone.

In this second aspect, when water is introduced into the second zone, the water can be introduced into the second zone upstream of the point of introduction of the feed mixture but downstream of the point of removal of the first extract stream, with respect to the flow of eluent in the second zone.

In this second aspect, the alcohol or aqueous alcohol can be introduced into the first zone upstream of the point of removal of the second extract stream, with respect to the flow of eluent in the first zone.

In this second aspect, when water is introduced into the first zone, the water can be introduced into the first zone upstream of the point of introduction of the first raffinate stream but downstream of the point of removal of the second extract stream, with respect to the flow of eluent in the first zone.

In a third aspect of the present invention, the simulated or actual moving bed chromatography apparatus consists of fifteen chromatographic columns. These are referred to as columns 1 to 15. The fifteen columns are arranged in series so that the bottom of column 1 is linked to the top of column 2, the bottom of column 2 is linked to the top of column 3 etc. This can optionally be via a holding container, with a recycle stream into the next column. The flow of eluent through the system is from column 1 to column 2 to column 3 etc. The flow of adsorbent through the system is from column 15 to column 14 to column 13 etc.

In a fourth aspect, the first zone typically consists of eight adjacent columns, columns 1 to 8, which are connected as discussed above. In this fourth aspect, the second zone typically consists of seven columns, columns 9 to 15, which are connected as discussed above. For the avoidance of doubt, the bottom of column 8 in the first zone is linked to the top of column 9 in the second zone.

In a another aspect, when one or more components exhibit a much stronger affinity for the stationary phase adsorbent (i.e., much slower running components) than the other components, the feed containing the LCDA is first introduced into a pre-treatment guard bed containing the stationary phase adsorbent to capture the much slower running components, forming a guard bed effluent of treated feed that is reduced in the much slower running components. The treated feed is subsequently introduced into a SMB unit to separate the LCDA from the other remaining components. In another aspect, two parallel guard beds are employed, where one guard bed is operating to adsorb the much slower running components in the feed and produce a treated feed, while the other guard bed does not receive a feed and is instead being regenerated by introducing a desorbent to desorb the much slower running components from the stationary phase.

In another aspect, the guard bed can be extracted with a solvent to remove the slower running components. If the slower running components such as monocarboxylic acids or hydroxyl acids are unreacted starting material or intermediates in the chemical or biological preparation of diacids, the recovered slower running components, after removal of unwanted solvents, may be recycled back to the chemical or biological processes.

In another aspect, the extract is fed to an extract desorbent recovery step to recover desorbent and produce a treated extract that is reduced in desorbent. The specific type of separation step will depend on the physical properties of the desorbent and other components in the extract. The extract desorbent recovery step can be selection from the non-limiting group comprising evaporation, distillation, crystallization, vacuum crystallization, and cooling crystallization. In one aspect, the desorbent that is recovered from the extract desorbent recovery step is recycled to the SMB unit. In another aspect, the components in the extract such as monocarboxylic acids or hydroxyl acids are unreacted starting material or intermediates in the preparation of diacids may be recycled back to the chemical or biological processes.

In another aspect, the raffinate is fed to a raffinate desorbent recovery step to recover desorbent and produce a treated raffinate that is reduced in desorbent. The specific type of separation step will depend on the physical properties of the desorbent and other components in the raffinate. The raffinate desorbent recovery step may comprise one for more separation unit operations selected from the non-limiting group comprising evaporation, distillation, vacuum distillation, filtration, membrane separation, crystallization, evaporative crystallization, and cooling crystallization. In one aspect, the desorbent that is recovered from the raffinate desorbent recovery step is recycled to the SMB unit.

In another aspect, the raffinate is fed to a water removal step to produce treated raffinate that is reduced in water. The specific type of water removal step will depend on the nature of the components in the raffinate. The water removal step may comprise one or more separation unit operations selected from the non-limiting group comprising evaporation, distillation, vacuum distillation, filtration, membrane separation, crystallization, evaporative crystallization, and cooling crystallization. In one aspect the water that is recovered from the water removal step is recycled to the SMB unit. In one aspect the water that is recovered from the water removal step is recycled to a fermentation step.

EXAMPLES

The invention is further described in the following examples, which do not limit the scope of the invention described in the claims.

Example 1—HPLC Tests

A 10 µL volume of feed mixture comprising a diacid, a monocarboxylic acid, and a hydroxyl acid in methanol, each at a concentration of 10 mg/mL, was injected into an HPLC column containing a stationary phase adsorbent of 5 µm particle size and 120 Å pore size. An aqueous methanol eluent (i.e., mobile phase) was then fed at a flow rate of 1 mL/min to the HPLC column (model HP-1100) operating at a set temperature. The eluent stream leaving the column was analyzed by continuous UV detection at 220 nm to determine the concentrations and retention times of the diacid, mono carboxylic acid, and hydroxyl acid species.

In examples 1a-1c, the diacid was adipic acid (AA), the monocarboxylic acid was caproic acid (CA), and the hydroxyl acid was 6-hydroxycaproic acid (6-HCA). In examples 1d-1e, the diacid was dodecandioc acid (DDDA), the monocarboxylic acid was lauric acid (LA), and the hydroxyl acid was 12-hydroxydodecanoic acid (12-DDA).

Specific feed mixture components, HPLC column dimensions, temperature, stationary phase, aqueous methanol eluent concentration and flow rate, and measured retention times (at peak concentration) of each component are tabulated in Table 1. Orpheus ADS1, Orpheus ADS2, and Orpheus ADS3 are non-polar silica-based stationary phase adsorbents available from Orochem Technologies Inc., Naperville, Ill., USA. Orpheus ADS2 is more non-polar than ADS1. Polar C18 non-polar adsorbent (but more polar than normal C18) is available from Orochem Technologies Inc., Naperville, Ill., USA.

TABLE 1

| Ex | Acid Components in Feed[1] | HPLC Column Diameter × Length, mm | HPLC Column Temperature, ° C. | Stationary Phase Adsorbent | Eluent (Mobile Phase) Methanol:Water (vol:vol) | Eluent Flow Rate, mL/min | Retention (Elution) Time, min |
|---|---|---|---|---|---|---|---|
| 1a | AA, 6-HCA, CA | 4 × 50 | 27 | Orpheus ADS1 | 50:50 | 1.0 | AA 2.61; 6-HCA 2.76; CA 9.00 |
| 1b | AA, 6-HCA, CA | 4 × 50 | 60 | Orpheus ADS2 | 11:89 | 1.0 | AA 9.07; 6-HCA 10.43; CA >60 |

TABLE 1-continued

| Ex | Acid Components in Feed[1] | HPLC Column Diameter × Length, mm | HPLC Column Temperature, °C. | Stationary Phase Adsorbent | Eluent (Mobile Phase) Methanol:Water (vol:vol) | Eluent Flow Rate, mL/min | Retention (Elution) Time, min |
|---|---|---|---|---|---|---|---|
| 1c | AA, 6-HCA, CA | 4.6 × 250 | 60 | Polar C18 | 5:95 | 1.0 | AA 12.4; 6-HCA 14.7; CA >30 |
| 1d | DDDA, 12-HDDA, LA | 4 × 50 | 27 | Orpheus ADS1 | 70:30 | 1.0 | DDDA 5.52; 12-HDDA 6.12; LA 36.27 |
| 1e | DDDA, 12-HDDA, LA | 4 × 50 | 27 | Orpheus ADS3 | 63:37 | 1.0 | DDDA 6.40; 12-HDDA 7.76; LA 35.65 |

Example 2—Pulse Tests

An aqueous methanol eluent (i.e., mobile phase) of methanol:water volumetric ratio varying from 95:5 to 80:20 vol:vol was fed at flow rate of 5 mL/min to a column of 10 mm diameter by 250 mm length, packed with Orpheus ADS adsorbent particles of 250-500 μm particle diameter, and maintained at 60° C. temperature. The mass of the adsorbent was approximately 12 g. The eluent flow was temporarily stopped, a 5 mL volume pulse of feed mixture was injected into the column, the eluent flow was restarted at a flow rate of 5 mL/min, the eluent leaving the column was collected as a series of 5 mL samples every 1 minute, and the samples were analyzed by mass spectrometer (API 3000 LC-MS/MS) to determine concentrations of the acid components as a function of time since feed injection.

Figure 11:
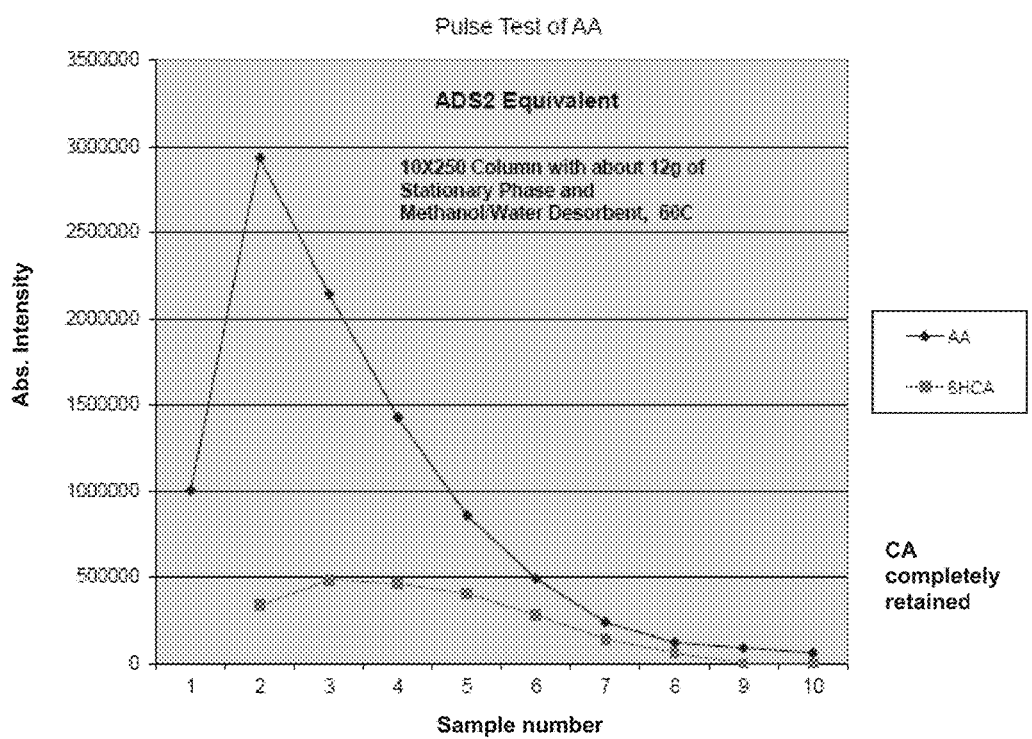
FIG. 11 illustrates an adsorption pulse test for a feed mixture comprising a C6 diacid.
Figure 12:
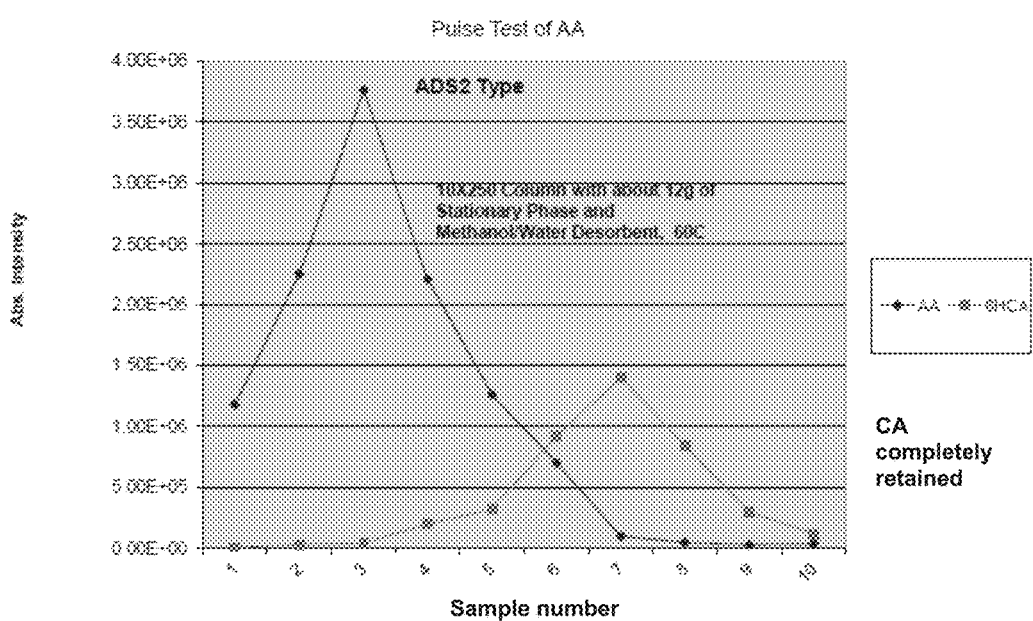
FIG. 12 illustrates an adsorption pulse test for a feed mixture comprising a C6 diacid.
Figure 13:
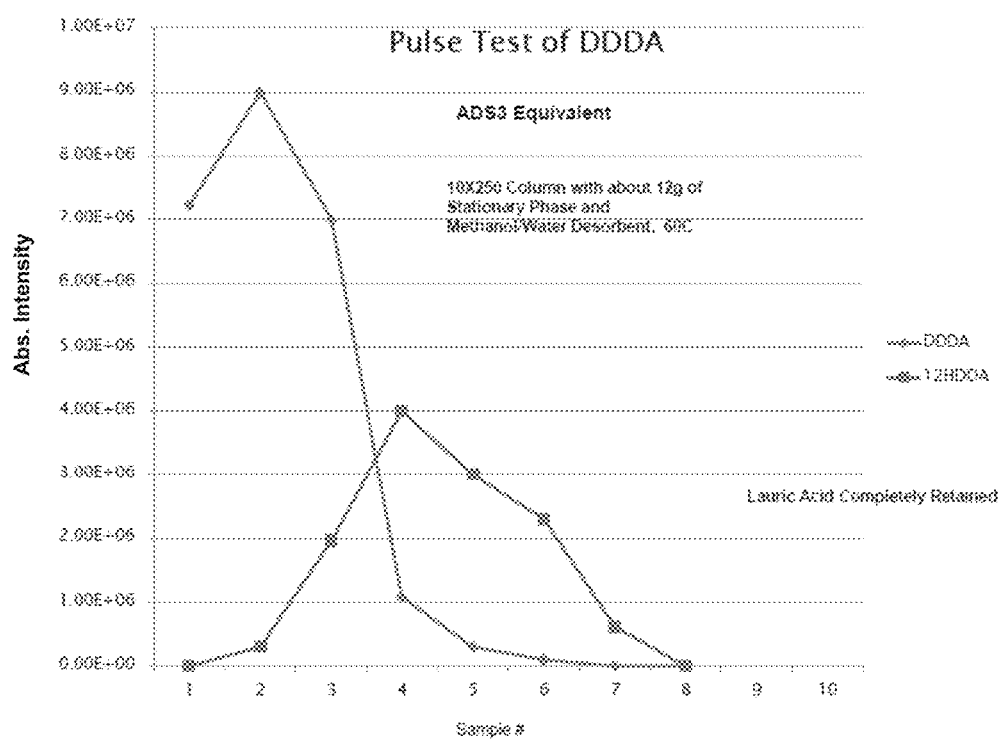
FIG. 13 illustrates an adsorption pulse test for a feed mixture comprising a C12 diacid.

In example 2a, the feed mixture composition was 10 wt % AA, 5 wt % 6-HCA, and 5 wt % CA in methanol; the adsorbent was Orpheus ADS2-equivalent (C18 22% C in FIG. 11; Polar C18 in FIG. 12); and the absorbance intensity of the eluted components in each collected sample is plotted in FIGS. 11 and 12. In example 2b the feed mixture composition was 10 wt % DDDA, 5 wt % 12-HDDA, and 5 wt % LA in methanol; the adsorbent was Orpheus ADS3-equivalent (C8); and the absorbance intensity of the eluted components in each collected sample is plotted in FIG. 13.

Example 3—SMB Separation of C6 Diacid

An aqueous feed mixture comprising 10 wt % adipic acid (AA), 0.5 wt % 6-hydroxycaproic acid (6-HCA), and 0.5 wt % caproic acid (CA) is fed at a flow rate of 145,874 kg/hr to a SMB unit comprising 15 columns and operating at 37° C. Each column contains an adsorbent bed 4 m in diameter by 4 m in height of Orpheus ADS2 non-polar silica-based stationary phase adsorbent of 250 μm particle size and 120 Å pore size, available from Orochem Technologies Inc., Naperville, Ill., USA. A methanol desorbent (mobile phase) is fed to the SMB unit at a flow rate of 52,083 kg/hr. An extract is withdrawn from the SMB unit at a flow rate of 40,968 kg/hr. A raffinate is withdrawn from the SMB unit at a flow rate of 156,989 kg/hr.

At a time t, the aqueous feed mixture is fed to column 10, the methanol desorbent is fed to column 1, the extract is withdrawn from column 6, and the raffinate is withdrawn from column 14. Periodically, according to a step time, dt, the inlet and outlet flows are each shifted to the next higher numbered column (i.e., in the direction of liquid flow), simulating an opposite movement of each stationary phase adsorbent bed to the next lower numbered column. Any inlet or outlet flow that was previously directed to or from column 15 moves to or from column 1. In other words, at time t+dt, the aqueous feed mixture is fed to column 11, the methanol desorbent is fed to column 2, the extract is withdrawn from column 7, and the raffinate is withdrawn from column 15. The total cycle time for the 15-column SMB unit is 15×dt.

The step time, dt, is adjusted to 10 minutes (600 seconds) so that, at steady-state, the composition of the extract is 1.7 wt % CA, 1.53 wt % 6-HCA, 1.7 wt % AA, 3.2 wt % water, and the remainder methanol; the composition of the raffinate is 0.02 wt % CA, 0.07 wt % 6-HCA, 8.85 wt % AA, 8.45 wt % methanol, and the remainder water; the AA recovery in the raffinate is 95.2% of the AA in the aqueous feed mixture; and AA purity in the raffinate is 99.0 wt % (on an acids-only basis).

Example 4—SMB Separation of C12 Diacid

An aqueous feed mixture comprising 10 wt % dodecandioic acid (DDDA), 0.5 wt % 12-hydroxydecanoic acid (12-HDDA), and 0.5 wt % lauric acid (LA) is fed at a flowrate of 29,167 kg/hr to a SMB unit comprising 15 columns and operating at 37° C. Each column contains an adsorbent bed 2 m in diameter by 3 m in height of Orpheus ADS3 non-polar silica-based stationary phase adsorbent of 250 μm particle size and 120 Å pore size, available from Orochem Technologies Inc., Naperville, Ill., USA. A methanol desorbent (mobile phase) is fed to the SMB unit at a flow rate of 12,188 kg/hr. An extract is withdrawn from the SMB unit at a flow rate of 10,034 kg/hr. A raffinate is withdrawn from the SMB unit at a flow rate of 31,320 kg/hr.

At a time t, the aqueous feed mixture is fed to column 10, the methanol desorbent is fed to column 1, the extract is withdrawn from column 6, and the raffinate is withdrawn from column 14. Periodically, according to a step time, dt, the inlet and outlet flows are each shifted to the next higher numbered column (i.e., in the direction of liquid flow), simulating an opposite movement of each stationary phase adsorbent bed to the next lower numbered column. Any inlet or outlet flow that was previously directed to or from column 15 moves to or from column 1. In other words, at time t+dt, the aqueous feed mixture is fed to column 11, the methanol desorbent is fed to column 2, the extract is withdrawn from column 7, and the raffinate is withdrawn from column 15. The total cycle time for the 15-column SMB unit is 15×dt.

The step time, dt, is adjusted so that, at steady-state, the composition of the extract is 1.5 wt % LA, 1.3 wt % 12-HDDA, 1.4 wt % DDDA, 0.3 wt % water, and the remainder methanol; the composition of the raffinate is 0 wt % LA, 0.04 wt % 12-HDDA, 8.85 wt % DDDA, 8.28 wt % methanol, and the remainder water; the DDDA recovery in the raffinate is 95.2% of the DDDA in the aqueous feed mixture; and the DDDA purity in the raffinate is 99.5 wt % (on an acids-only basis).

What is claimed is:

1. A method for separating a C6- to C18-carbon diacid from at least one impurity in a solution, the method comprising either:
   (1) (a) introducing a feed stream comprising a solution comprising at least one 6- to 18-carbon diacid and at least one impurity, the at least one impurity comprising at least one component more polar than the diacid, at least one component less polar than the diacid, or at least one component more polar than the diacid and at least one component less polar than the diacid, into a first zone of moving bed chromatography apparatus (MBCA) having one or more zones, wherein each zone comprises at least one adsorbent stationary phase,
   (b) collecting a raffinate stream or an extract stream from the first zone of the MBCA, the raffinate stream comprising the diacid and at least one component more polar than the diacid, and the extract stream comprising the diacid and at least one component less polar than the diacid,
   (c) introducing the raffinate stream or the extract stream into a second zone of the MBCA,
   (d) collecting a second raffinate stream or a second extract stream from the second zone of the MBCA, the raffinate stream comprising the diacid and at least one component more polar than the diacid, and the extract stream comprising the diacid and at least one component less polar than the diacid,
   (e) introducing the second raffinate stream or the second extract stream into the first zone or the second zone of the MBCA,
   (f) optionally repeating steps (d) and (e) until a desired degree of separation is achieved, and
   (g) collecting a final raffinate stream or a final extract stream from a zone the MBCA, the final raffinate stream or the extract stream comprising the diacid, thereby separating a C6- to C18-carbon diacid from the at least one impurity in the solution; or
   (2) (a) introducing a feed stream comprising a solution comprising at least one 6- to 18-carbon diacid and at least one impurity, the at least one impurity comprising at least one component more polar than the diacid, at least one component less polar than the diacid, or at least one component more polar than the diacid and at least one component less polar than the diacid, into a first zone of a moving bed chromatography apparatus (MBCA), wherein the first zone comprises at least one adsorbent stationary phase,
   (b) collecting a raffinate stream or an extract stream from the MBCA, the raffinate stream comprising the diacid and at least one component more polar than the diacid, and the extract stream comprising the diacid and at least one component less polar than the diacid,
   (c) introducing the raffinate stream or the extract stream into the first zone of the MBCA,
   (d) optionally repeating steps (b) and (c) until a desired degree of separation is achieved, and
   (e) collecting a final raffinate stream or a final extract stream from the first zone of the MBCA, the final raffinate stream or the extract stream comprising the diacid, thereby separating a C6- to C18-carbon diacid from the solution.

2. The method of claim 1, wherein the at least one impurity is present in a final raffinate stream or a final extract stream at 10,000 ppmw or less, 5,000 ppmw or less, 1,000 ppmw or less, 500 ppmw or less, 100 ppmw or less, 50 ppmw or less, or 10 ppmw or less.

3. The method of claim 1, further comprising introducing the raffinate stream or the extract stream into the first zone of the MBCA prior to the first raffinate stream or the first extract stream and introducing the raffinate stream or the extract stream into the second zone of the MBCA.

4. The method of claim 1, wherein the MBCA comprises two or more zones, each zone comprising:
   one or more injection points for introducing the solution;
   one or more injection points for introducing an eluent;
   a raffinate stream from which liquid can be collected; and
   an extract stream from which liquid can be collected.

5. The method of claim 1, wherein the at least one impurity is:
   (a) a monocarboxylic acid, an alkane, or a hydroxyl acid;
   (b) more polar than the 6- to 18-carbon diacid; and/or
   (c) less polar than the 6- to 18-carbon diacid.

6. The method of claim 1, wherein the at least one 6- to 18-carbon diacid is:
   (a) an α, ω diacid;
   (b) an alkane diacid or an olefin diacid;
   (c) selected from a C6 diacid (adipic acid), C7 diacid (pimelic acid), C8 diacid (suberic acid), C9 diacid (azelaic acid), C10 diacid (sebacic acid), C11 diacid (undecanedioic acid), C12 diacid (dodecanedioic acid), C13 diacid (tridecanedioic acid), C14 diacid (tetradecanedioic acid), C15 diacid (pentadecanedioic acid), C16 diacid (hexadecanedioic acid), C17 diacid (heptadecanedioic acid), C18 diacid (octadecanedioic acid), and C6-18-olefin diacid;
   (d) produced by chemical means; and/or
   (e) a bioderived compound produced by fermentation.

7. The method of claim 1, wherein the solution comprises a fermentation broth from a biological mixture.

8. The method of claim 1, wherein the MBCA comprises three to fifteen chromatography columns.

9. The method of claim 1, wherein the apparatus comprises:
   (a) two or more zones;
   (b) two zones, the eluent in the first zone containing more alcohol than the eluent in the second zone, and the second zone is downstream of the first zone with respect to the flow of eluent in the system; and/or
   (c) a first zone, a second zone, and a third zone, the eluent in the first zone containing more alcohol than the eluent in the second zone and the third zone and the first zone is upstream of the second and third zones with respect to the flow of eluent in the system, and the eluent in the second zone contains more alcohol than the eluent in the third zone and the second zone is upstream of the third zone with respect to the flow of eluent in the system.

10. The method of claim 1, wherein the eluent comprises an aqueous alcohol.

11. The method of claim 1, wherein the C6- to C18-carbon diacid recovery is at least 80%, at least 82%, at least 85%, at least 88%, at least 90%, at least 91%, at least 92%, at least 93%, at least 94%, at least 95%, at least 96%, at least 97%, at least 98%, at least 99%, or at least 99.9% relative to the amount of the at least one impurity.

12. A method for obtaining a diacid comprising:
   (a) providing a solution comprising at least one C6- to C18-carbon diacid and at least one impurity,
   (b) introducing the solution into a moving bed chromatography apparatus (MBCA) having one or more chromatography columns and at least one eluent, wherein at least one chromatography column comprises an adsorbent stationary phase, (c) producing a raffinate and an extract, and (d) recovering a purified C6- to C18-carbon diacid composition from the raffinate or the extract, or both, wherein said at least one impurity is present in the purified diacid composition at 10,000 ppmw or less, 5,000 ppmw or less, 1,000 ppmw or less, 500 ppmw or less, 100 ppmw or less, 50 ppmw or less, or 10 ppmw or less.

13. The method of claim 12, wherein the C6- to C18-carbon diacid recovery is at least 80%, at least 82%, at least 85%, at least 88%, at least 90%, at least 91%, at least 92%, at least 93%, at least 94%, at least 95%, at least 96%, at least 97%, at least 98%, at least 99%, or at least 99.9% relative to the amount of the at least one impurity.

14. A method for separating adipic acid from 6-hydroxycaproic acid and caproic acid in a solution, the method comprising:

(a) introducing a feed stream comprising a solution comprising adipic acid, 6-hydroxycaproic acid, and caproic acid into a first zone of moving bed chromatography apparatus (MBCA), wherein the first zone comprises at least one adsorbent stationary phase;

(b) collecting a raffinate stream or an extract stream from the first zone of the MBCA, the raffinate stream comprising the adipic acid and 6-hydroxycaproic acid, and the extract stream comprising the adipic acid and caproic acid;

(c) introducing the raffinate stream or the extract stream into a second zone of the MBCA;

(d) collecting a second raffinate stream or a second extract stream from the second zone of the MBCA, the raffinate stream comprising the adipic acid and 6-hydroxycaproic acid, and the extract stream comprising the adipic acid and caproic acid;

(e) introducing the second raffinate stream or the second extract stream into the first zone or the second zone of the MBCA;

(f) optionally repeating steps (d) and (e) until a desired degree of separation is achieved; and (g) collecting a final raffinate stream or a final extract stream from a zone of the MBCA, the final raffinate stream or the extract stream comprising the adipic acid, thereby separating the adipic acid from the 6-hydroxycaproic acid and caproic acid.

15. A method for separating dodecandioic acid from 12-hydroxydecanoic acid and lauric acid in a solution, the method comprising:

(a) introducing a feed stream comprising a solution comprising dodecandioic acid, 12-hydroxydecanoic acid, and lauric acid into a first zone of moving bed chromatography apparatus (MBCA), wherein the first zone comprises at least one adsorbent stationary phase;

(b) collecting a raffinate stream or an extract stream from the first zone of the MBCA, the raffinate stream comprising the dodecandioic acid and 12-hydroxydecanoic acid, and the extract stream comprising the dodecandioic acid and lauric acid;

(c) introducing the raffinate stream or the extract stream into a second zone of the MBCA;

(d) collecting a second raffinate stream or a second extract stream from the second zone of the MBCA, the raffinate stream comprising the dodecandioic acid and 12-hydroxydecanoic acid, and the extract stream comprising the dodecandioic acid and lauric acid;

(e) introducing the second raffinate stream or the second extract stream into the first zone or the second zone of the MBCA;

(f) optionally repeating steps (d) and (e) until a desired degree of separation is achieved; and (g) collecting a final raffinate stream or a final extract stream from a zone of the MBCA, the final raffinate stream or the extract stream comprising the dodecandioic acid, thereby separating the dodecandioic acid from the 12-hydroxydecanoic acid and lauric acid.

* * * * *